US010201587B2

(12) United States Patent
Neesham-Grenon et al.

(10) Patent No.: US 10,201,587 B2
(45) Date of Patent: Feb. 12, 2019

(54) METHODS OF INHIBITING AND TREATING BIOFILMS USING GLYCOPEPTIDE ANTIBIOTICS

(75) Inventors: Eve Neesham-Grenon, Montreal (CA); Gregory Moeck, St. Laurent (CA); Adam Belley, Beaconsfield (CA); Thomas R. Parr, Jr., Indianapolis, IN (US); Adel Rafai Far, Mount-Royal (CA)

(73) Assignee: MELINTA THERAPEUTICS, INC., New Haven, CT (US)

( * ) Notice: Subject to any disclaimer, the term of this patent is extended or adjusted under 35 U.S.C. 154(b) by 0 days.

(21) Appl. No.: 12/936,722

(22) PCT Filed: Apr. 2, 2009

(86) PCT No.: PCT/US2009/039240
§ 371 (c)(1),
(2), (4) Date: Nov. 2, 2010

(87) PCT Pub. No.: WO2009/126502
PCT Pub. Date: Oct. 15, 2009

(65) Prior Publication Data
US 2011/0046041 A1 Feb. 24, 2011

Related U.S. Application Data

(60) Provisional application No. 61/043,301, filed on Apr. 8, 2008.

(51) Int. Cl.
*A61K 38/14* (2006.01)
*A61P 31/04* (2006.01)
*A61K 45/06* (2006.01)

(52) U.S. Cl.
CPC .............. *A61K 38/14* (2013.01); *A61K 45/06* (2013.01)

(58) Field of Classification Search
CPC ..... A61K 38/14; A61K 45/06; A61K 2300/00
See application file for complete search history.

(56) References Cited

U.S. PATENT DOCUMENTS

| | | | | |
|---|---|---|---|---|
| 7,442,762 | B2 * | 10/2008 | Severinov et al. | 530/326 |
| 7,612,045 | B2 * | 11/2009 | Eldridge | 514/31 |
| 8,518,873 | B2 * | 8/2013 | Wilcox et al. | 514/2.9 |
| 2003/0176327 | A1 * | 9/2003 | Cassell et al. | 514/8 |
| 2003/0229000 | A1 * | 12/2003 | Merritt | A61K 38/1709 514/1 |
| 2003/0236265 | A1 | 12/2003 | Sayada | |
| 2004/0147441 | A1 | 7/2004 | Leach et al. | |
| 2004/0147595 | A1 * | 7/2004 | Kjelleberg | A01N 43/08 514/463 |
| 2005/0271694 | A1 | 12/2005 | Mansouri et al. | |
| 2007/0173438 | A1 | 7/2007 | Boger et al. | |

FOREIGN PATENT DOCUMENTS

| | | |
|---|---|---|
| WO | 08/097364 | 8/2008 |
| WO | 09/036121 | 3/2009 |

OTHER PUBLICATIONS

Targata Therapeutics, May 2007.*
Lee et al. Microbiology 2007.*
Schuch et al. PLOS one Published on Aug. 12, 2009 e6532.*
Mercier et al. (Journal Antimicrobial Chemotherapy (2002) 50, 19-24).*
Belley et al. (47th ICAA Chicago, , Wednesday Session, 175 E, Sep. 17-20, 2007, E-1619).*
Belley et al. (47th ICAA Chicago, Wednesday Session, 175 E, Sep. 17-20, 2007, E-1620).*
Wilcox (Abstract, 47th ICAA Chicago, , Wednesday Session, 175 E, Sep. 17-20, 2007, E1618).*
Crowther et al., Abstract, PLOS ONE, www.plosone.org, Feb. 1, 2014, vol. 9, Issue 2, e88396).*
Gander et al. (Conference Abstract 43rd Annual Interscience Conference on Antimicrobial Agents and Chemotherapy, Sep. 14-17, 2003 vol. 43 pp. 264).*
Rifamycins, from http://www.uptodate.com/contents/rifamycins-rifampin-rifabutin-rifapentine, pp. 1-4, accessed Apr. 28, 2016.*
Romling et al, Biofilm infections, their resilience to therapy and innovative treatment strategies, J Intern Med, 2012, 272, pp. 541-561.*
Wu et al, Strategies for combating bacterial biofilm infections, International Journal of Oral Science, 2015, 7, pp. 1-7.*
Carmen et al, Ultrasonically Enhanced Vancomycin Activity Against *Staphylococcus epidermidis* Biofilms In Vivo, Journal of Biomaterials Applications, 2004, 18, pp. 237-245.*
Kadurugamuwa et al, Rapid Direct Method for Monitoring Antibiotics in a Mouse Model of Bacterial Biofilm Infection, Antimicrobial Agents and Chemotherapy, 2003, 47, pp. 3130-3137.*
Murphy et al, In Vitro Activity of Novel Rifamycins against Rifamycin-Resistant *Staphylococcus aureus*, Antimicrobial Agents and Chemotherapy, 2006, 50, pp. 827-834.*
Lebeaux et al, From in vitro to in vivo Models of Bacterial Biofilm-Related Infections, Pathogens, 2013, 2, pp. 288-356.*
International Search Report and Written Opinion of PCT/US09/039240 dated May 18, 2009.
Supplementary European Search Report from EP Appln. No. 09731140, dated Jul. 30, 2013.

(Continued)

*Primary Examiner* — Julie Ha
*Assistant Examiner* — Li N Komatsu
(74) *Attorney, Agent, or Firm* — Wenderoth, Lind & Ponack, L.L.P.

(57) ABSTRACT

The present invention is directed to methods of inhibition, delay of formation, treatment, prophylaxis and/or prevention of infections caused by bacteria that exhibit tolerance to antimicrobial agents, including slow growing, stationary-phase and biofilm forming bacteria, through the use of glycopeptide antibiotics, such as oritavancin.

8 Claims, 6 Drawing Sheets

(56) References Cited

OTHER PUBLICATIONS

Gander et al. The effect of the novel glycopeptide, TD-6424, on biofilms of susceptible and resistant *staphylococci*. Abstracts of the Interscience Conference on Antimicrobial Agents and Chemotherapy, vol. 43, 2003, p. 264, 43rd Annual Interscience Conference on Antimicrobial Agents and Chemotherapy; Chicago, IL, USA; Sep. 14-17, 2003.

Belley et al., Oritavancin Kills *Staphylococcus aureus* in Slow-Growing Planktonic and Biofilm States.,Abstracts of the Interscience Conference on Antimicrobial Agents and Chemotherapy, vol. 46, 2006, p. 42, 46th Interscience Conference on Antimicrobial Agents and Chemotherapy; San Francisco, CA, USA; Sep. 27-30, 2006.

Heine et al. Efficacy of oritavancin in a murine model of Bacillus anthracis spore inhalation anthrax. Abstracts of the General Meeting of the American Society for Microbiology, Washington, DC : American Society for Microbiology, 2000, US, vol. 107, Jan. 1, 2007, p. 23.

Poulakou G. et al. Oritavancin: A new promising agent in the treatment of infections due to Gram-positive pathogens. Expert Opinion on Investigational Drugs, vol. 17, No. 2, Feb. 2008, pp. 225-243.

\* cited by examiner

METHODS OF INHIBITING AND TREATING BIOFILMS USING GLYCOPEPTIDE ANTIBIOTICS

TECHNICAL FIELD

The present invention is directed to methods of inhibition, delay of formation, treatment, prophylaxis and/or prevention of infections caused by bacteria that exhibit tolerance to antimicrobial agents, including slow growing, stationary-phase and biofilm forming bacteria (e.g., dormant bacteria), through the use of glycopeptide antibiotics, such as oritavancin.

BACKGROUND OF THE TECHNOLOGY

Infections in which bacteria are either slow-growing, dormant or in a biofilm pose a serious clinical challenge for therapy because cells in these states exhibit tolerance to the activity of most antimicrobial agents (12). Osteomyelitis, infective endocarditis, chronic wounds and infections related to indwelling devices are examples of infections that harbor tolerant cells (7, 13). Because most antimicrobial agents exert maximal activity against rapidly dividing cells, antimicrobial therapies for these infections are not optimal, requiring protracted treatment times and demonstrating higher failure rates.

A model theory has been proposed to explain biofilm recalcitrance to chemotherapy (24): the diversity of the growth phases of the biofilm community and the composition of the slime matrix act to limit the effectiveness of otherwise useful antimicrobial agents. It is believed that a population of slow-growing, stationary-phase or 'persister' cells within the biofilm can tolerate the killing action of antibacterial agents. This has been demonstrated with the fluoroquinolone antibiotic ofloxacin in which a small population of cells within a biofilm were not killed by this agent (41). Furthermore, it is thought these tolerant cells are protected from immune clearance in vivo by the biofilm slime matrix and ultimately give rise to relapse infections by reseeding the biofilm once drug levels drop below their antibacterial concentration (24).

Oritavancin is a semi-synthetic lipoglycopeptide in clinical development against serious gram-positive infections. It exerts activity against methicillin-resistant *Staphylococcus aureus* (MRSA) and vancomycin-resistant enterococci (VRE). The rapidity of its bactericidal activity against exponentially-growing *S. aureus* (≥3-log reduction within 15 minutes to 2 hours against MSSA, MRSA, and VRSA) is one feature that distinguishes it from the prototypic glycopeptide vancomycin (29). Recent work demonstrated that oritavancin has multiple mechanisms of action that can contribute to cell death of exponentially-growing *S. aureus*, including inhibition of cell wall synthesis by both substrate-dependent and -independent mechanisms (2, 4, 45), disruption of membrane potential and increasing membrane permeability (30), and inhibition of RNA synthesis (4). The ability of oritavancin but not vancomycin to interact with the cell membrane, leading to loss of membrane integrity and collapse of transmembrane potential, correlates with the rapidity of oritavancin bactericidal activity (30). Mechanisms of action beyond substrate-dependent cell wall synthesis inhibition have not been described to date for vancomycin; consequently, vancomycin typically requires 24 h and actively dividing cells to exert bactericidal activity (Belley ICAAC 2006 stat phase poster; Belley 2007 ICAAC stat phase poster; (29)).

There is a need for new methods of treatment for bacteria in slow-growing, stationary-phase and biofilm states.

SUMMARY

As disclosed herein, it has been discovered that the glycopeptide antibiotic oritavancin, also known in the art and referred to herein as $N^{DISACC}$-(4-(4-chlorophenyl)benzyl) A82846B and LY333328, demonstrates significant activity against bacteria that exhibit tolerance to antimicrobial agents. In particular, oritavancin shows activity against dormant bacteria such as: (i) slow growing, (ii) stationary-phase and (iii) biofilm forms of *Staphylococcus aureus*, *Staphylococcus epidermidis*, and both vancomycin susceptible- and resistant enterococci. The results of the experiments described herein demonstrate that glycopeptide antibiotics, such as oritavancin (or its pharmaceutically acceptable salts, hydrates, or solvates thereof, as well as mixtures thereof), will be efficacious in the inhibition, delay of formation, treatment, prophylaxis and/or prevention of infections by dormant bacteria, including infections of slow growing, stationary-phase or biofilm forming bacteria in animals, including humans.

Inhibition

The invention is generally directed to methods of inhibiting the growth of dormant bacteria, comprising contacting dormant bacteria with a glycopeptide antibiotic in an amount sufficient to inhibit the growth of the dormant bacteria, wherein the dormant bacteria is one or more of: (i) slow growing bacteria, (ii) stationary-phase bacteria and (iii) bacteria in biofilm form.

In one embodiment, the invention is directed to methods of inhibiting an infection caused by dormant bacteria in a subject, comprising administering a therapeutically effective amount of a glycopeptide antibiotic to a subject having an infection caused by dormant bacteria, wherein the dormant bacteria is one or more of: (i) slow growing bacteria, (ii) stationary-phase bacteria and (iii) a bacteria in biofilm. In these embodiments the dormant bacteria may be contacted with the glycopeptide antibiotic in vitro, in vivo and/or ex vivo.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In a further embodiment, the invention is directed to methods of inhibiting the formation of a biofilm on a surface or on a porous material, comprising applying a glycopeptide antibiotic to a surface or to a porous material upon which a biofilm may form in an amount sufficient to inhibit the formation of a biofilm. In preferred embodiments, the surface is an inert surface, such as the surface of an in-dwelling medical device.

In an additional embodiment, the invention is directed to methods of delaying the formation of a biofilm on a surface or on a porous material, comprising applying a glycopeptide antibiotic to a surface or to a porous material upon which a biofilm may form in an amount sufficient to delay the formation of a biofilm. In preferred embodiments, the surface is an inert surface, such as the surface of an in-dwelling medical device.

In each embodiment, the slow growing, stationary-phase or biofilm bacteria is any bacterial species that can exist in a slow growing or stationary-phase, or that can form a biofilm. In preferred embodiments, the bacteria is *Staphy-* lococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Treatment

The invention is also generally directed to methods of treating an infection caused by dormant bacteria in a subject, comprising administering a therapeutically effective amount of a glycopeptide antibiotic to a subject having an infection caused by dormant bacteria, wherein the dormant bacteria is one or more of: (i) slow growing bacteria, (ii) stationary-phase bacteria and (iii) bacteria in biofilm form. The dormant bacteria may be contacted with the glycopeptide antibiotic in vitro, in vivo and/or ex vivo.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Prevention

The invention is further generally directed to methods of preventing an infection caused by dormant bacteria in a subject, comprising administering to a subject at risk of developing an infection caused by dormant bacteria an amount of a glycopeptide antibiotic sufficient to prevent the infection, wherein the dormant bacteria is one or more of: (i) slow growing bacteria, (ii) stationary-phase bacteria and (iii) bacteria in biofilm form. The dormant bacteria may be contacted with the glycopeptide antibiotic in vitro, in vivo and/or ex vivo.

In one embodiment, the invention is directed to methods of preventing the formation of a biofilm in a subject, comprising administering to a subject at risk of biofilm formation an amount of a glycopeptide antibiotic sufficient to prevent biofilm formation.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In a further embodiment, the invention is directed to methods of preventing the formation of a biofilm on a surface or on a porous material, comprising applying a glycopeptide antibiotic in an amount sufficient to prevent the formation of a biofilm to a surface or on a porous material upon which a biofilm may form in an amount sufficient to prevent the formation of a biofilm. In preferred embodiments, the surface is an inert surface, such as the surface of an in-dwelling medical device.

The invention is also directed to methods of preventing the colonization of a surface by dormant bacteria, comprising applying a glycopeptide antibiotic to a surface in an amount sufficient to prevent colonization of the surface by a dormant bacteria, wherein the dormant bacteria is one or more of slow growing bacteria, stationary-phase bacteria and bacteria in biofilm form.

The invention is further directed to methods of preventing the colonization of a porous material by dormant bacteria, comprising applying a glycopeptide antibiotic to a porous material in an amount sufficient to prevent colonization of the porous material by a dormant bacteria, wherein the dormant bacteria is one or more of slow growing bacteria, stationary-phase bacteria and bacteria in biofilm form.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Prophylaxis

The invention is additionally generally directed to methods for providing prophylaxis of an infection caused by dormant bacteria in a subject, comprising administering to a subject having an infection caused by dormant bacteria an amount of a glycopeptide antibiotic sufficient to achieve prophylaxis of the infection, wherein the dormant bacteria is one or more of: (i) slow growing bacteria, (ii) stationary-phase bacteria and (iii) bacteria in biofilm form.

Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Devices

The invention is also generally directed to a surface comprising a glycopeptide antibiotic in an amount sufficient to inhibit the growth of one or more of: (i) slow growing bacteria, (ii) stationary-phase bacteria and (iii) bacteria in biofilm form. In one embodiment, the surface is an inert surface, such as the surface of an in-dwelling medical device. In preferred embodiments, the surface is coated by or impregnated with the glycopeptide antibiotic.

The invention is also generally directed to an in-dwelling medical device coated by or impregnated with a glycopeptide antibiotic in an amount sufficient to inhibit the growth of one or more of: (i) slow growing bacteria, (ii) stationary-phase bacteria and (iii) bacteria in biofilm form. In a preferred embodiment, a surface of the in-dwelling medical device is coated by or impregnated with the glycopeptide antibiotic.

The invention is further generally directed to a porous material comprising a glycopeptide antibiotic in an amount sufficient to inhibit the growth of one or more of: (i) slow growing bacteria, (ii) stationary-phase bacteria and (iii) bacteria in biofilm form. In preferred embodiments, the surface is coated by or impregnated with the glycopeptide antibiotic. Preferably, the glycopeptide antibiotic is oritavancin, or a pharmaceutically acceptable salt, hydrate, or solvate thereof, or a mixture thereof.

Uses

The present invention also includes the use of a glycopeptide antibiotic in the manufacture of a medicament for inhibition, delay of formation, treatment, prophylaxis and/or prevention of one or more of: a (i) slow growing, (ii) stationary-phase or (iii) biofilm bacterial infection in a subject or on a surface. Preferably, said glycopeptide antibiotic is oritavancin, or pharmaceutically acceptable salt, hydrate, or solvate thereof, or a mixture thereof.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

DETAILED DESCRIPTION

Figure 1:
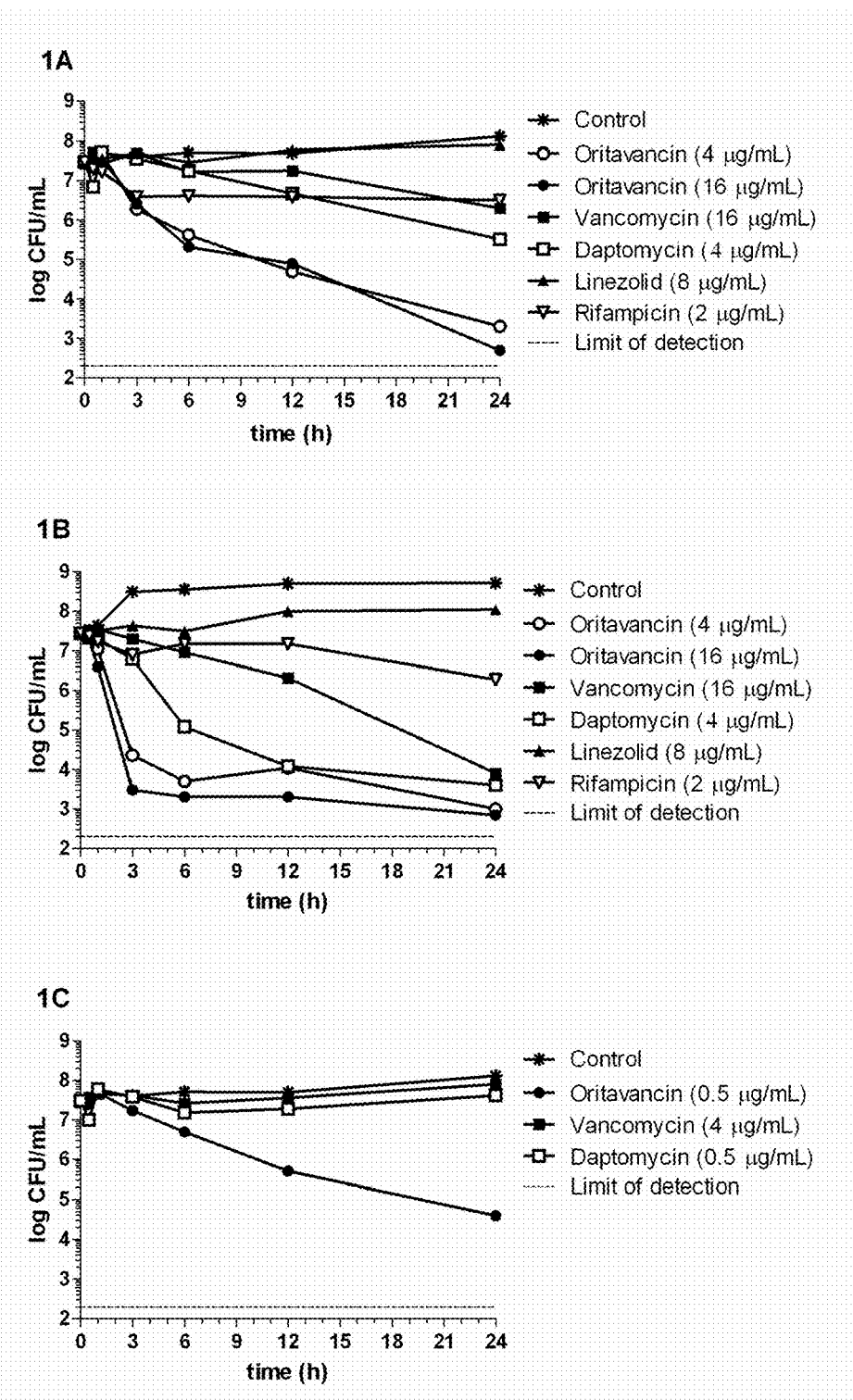
FIG. 1. Time-kill kinetics of MSSA ATCC 29213 at estimated $fC_{max}$ and free trough concentrations of oritavancin and comparators in nutrient-depleted CAMHB. Viability was enumerated at the indicated time points by serial dilution plating. Each point represents the mean of duplicate determinations. The limit of detection is indicated (- - -). A. Stationary-phase inocula with estimated $fC_{max}$ of oritavancin and comparators. B. Exponential-phase inocula with estimated $fC_{max}$ of oritavancin and comparators. For panels A and B: *, untreated control; ○, 4 μg/mL oritavancin; ●, 16 μg/mL oritavancin; ■, 16 μg/mL vancomycin; □, 4 μg/mL daptomycin; ▲, 8 μg/mL linezolid; ▽, 2 μg/mL rifampicin. C. Stationary-phase inocula with estimated free trough concentrations of oritavancin and comparators. *, untreated control; ●, 0.5 μg/mL oritavancin; ■, 4 μg/mL vancomycin; □, 0.5 μg/mL daptomycin.

The present invention is directed to methods of inhibition, delay of formation, treatment, prophylaxis and/or prevention of infections by dormant bacteria, including bacterial infections caused by slow growing, stationary-phase or biofilm forming bacteria in animals, including humans, through the use of glycopeptide antibiotics, such as oritavancin, and pharmaceutical compositions comprising glycopeptide antibiotics.

Inhibition

In particular, the invention is generally directed to methods of inhibiting the growth of dormant bacteria, comprising contacting dormant bacteria with a glycopeptide antibiotic in an amount sufficient to inhibit the growth of the dormant bacteria, wherein the dormant bacteria is one or more of: (i) slow growing bacteria, (ii) stationary-phase bacteria and (iii) bacteria in biofilm form. The dormant bacteria may be contacted with the glycopeptide antibiotic in vitro, in vivo and/or ex vivo.

The skilled artisan will understand that the methods of inhibition of the present invention can be practiced wherever dormant bacteria, such as slow growing, stationary-phase or biofilm forming bacteria, may be encountered. For example, the methods may be practice on the surface of or inside of an animal, such as a human, on a inert surface, such as a counter or bench top, on a surface of a piece of medical or laboratory equipment, on a surface of a medical or laboratory tool, or on a surface of an in-dwelling medical device.

In one embodiment, the invention is directed to methods of inhibiting an infection caused by dormant bacteria in a subject, comprising administering a therapeutically effective amount of a glycopeptide antibiotic to a subject having an infection caused by dormant bacteria, wherein the dormant bacteria is one or more of: (i) slow growing bacteria, (ii) stationary-phase bacteria and (iii) bacteria in biofilm. The dormant bacteria may be contacted with the glycopeptide antibiotic in vitro, in vivo and/or ex vivo.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In the preferred embodiments, the glycopeptide antibiotic is administered to the subject via intravenous administration or oral administration.

In each of the methods of inhibiting the growth of dormant bacteria, the dormant bacteria may be contacted with a second antibiotic concurrent with the glycopeptide antibiotic or a second antibiotic may be administered concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In a further embodiment, the invention is directed to methods of inhibiting the formation of a biofilm on a surface or on a porous material, comprising applying a glycopeptide antibiotic to a surface or to a porous material upon which a biofilm may form in an amount sufficient to inhibit the formation of a biofilm. In preferred embodiments, the surface is an inert surface, such as the surface of an in-dwelling medical device.

In an additional embodiment, the invention is directed to methods of delaying the formation of a biofilm on a surface or on a porous material, comprising applying a glycopeptide antibiotic in an amount sufficient to delay the formation of a biofilm to a surface or to a porous material upon which a biofilm may form in an amount sufficient to delay the formation of a biofilm. In preferred embodiments, the surface is an inert surface, such as the surface of an in-dwelling medical device.

In the embodiments of the invention directed to methods of inhibiting or delaying the formation of a biofilm, the material comprising the surface or the porous material may be any material that can be used to form a surface or a porous material. In preferred embodiments, the material is selected from the group of consisting of polyethylene, polytetrafluoroethylene, polypropylene, polystyrene, polyacrylamide, polyacrylonitrile, poly(methyl methacrylate), polyamide, polyester, polyurethane, polycarbornate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

The glycopeptide antibiotic may be bound to the surface or porous material through a non-covalent interaction or a covalent interaction.

In each of the methods of inhibiting or delaying the formation of a biofilm, a second antibiotic may be applied concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus*, *Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Treatment

The invention is also generally directed to methods of treating an infection caused by dormant bacteria in a subject, comprising administering a therapeutically effective amount of a glycopeptide antibiotic to a subject having an infection caused by dormant bacteria, wherein the dormant bacteria is one or more of: (i) slow growing bacteria, (ii) stationary-phase bacteria and (iii) bacteria in biofilm form. The dormant bacteria may be contacted with the glycopeptide antibiotic in vitro, in vivo and/or ex vivo.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In the preferred embodiments, the glycopeptide antibiotic is administered to the subject via intravenous administration or oral administration.

In each of the methods of treatment, a second antibiotic may be administered concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Prevention

The invention is further generally directed to methods of preventing an infection caused by dormant bacteria in a subject, comprising administering to a subject at risk of developing an infection caused by dormant bacteria an amount of a glycopeptide antibiotic sufficient to prevent the infection, wherein the dormant bacteria is one or more of: a (i) slow growing bacteria, (ii) stationary-phase bacteria and (iii) bacteria in biofilm form. The dormant bacteria may be contacted with the glycopeptide antibiotic in vitro, in vivo and/or ex vivo.

In one embodiment, the invention is directed to methods of preventing the formation of a biofilm in a subject, comprising administering to a subject at risk of biofilm formation an amount of a glycopeptide antibiotic sufficient to prevent biofilm formation.

Preferably, the glycopeptide antibiotic is administered to a subject in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In the preferred embodiments, the glycopeptide antibiotic is administered to the subject via intravenous administration or oral administration.

In each of the methods of preventing an infection caused by dormant bacteria or preventing the formation of a biofilm in a subject, a second antibiotic may be administered concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In a further embodiment, the invention is directed to methods of preventing the formation of a biofilm on a surface or on a porous material, comprising applying a glycopeptide antibiotic to a surface or on a porous material upon which a biofilm may form in an amount sufficient to prevent the formation of a biofilm. In preferred embodiments, the surface is an inert surface, such as the surface of an in-dwelling medical device.

In embodiments directed to preventing the formation of a biofilm on a surface or on a porous material, the material comprising the surface or the porous material may be any material that can be used to form a surface or a porous material. In preferred embodiments, the material is selected from the group of consisting of polyethylene, polytetrafluoroethylene, polypropylene, polystyrene, polyacrylamide, polyacrylonitrile, poly(methyl methacrylate), polyamide, polyester, polyurethane, polycarbornate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

The invention is also directed to methods of preventing the colonization of a surface by dormant bacteria, comprising applying a glycopeptide antibiotic to a surface in an amount sufficient to prevent colonization of the surface by dormant bacteria, wherein the dormant bacteria is one or more of slow growing bacteria, stationary-phase bacteria and bacteria in biofilm form.

The invention is further directed to methods of preventing the colonization of a porous material by dormant bacteria, comprising applying a glycopeptide antibiotic to a porous material in an amount sufficient to prevent colonization of the porous material by dormant bacteria, wherein the dormant bacteria is one or more of slow growing bacteria, stationary-phase bacteria and bacteria in biofilm form.

In embodiments directed to methods of preventing the colonization of a surface or a porous material, the material comprising the surface or the porous material may be any material that can be used to form a surface or a porous material. In preferred embodiments, the material is selected from the group of consisting of polyethylene, polytetrafluoroethylene, polypropylene, polystyrene, polyacrylamide, polyacrylonitrile, poly(methyl methacrylate), polyamide, polyester, polyurethane, polycarbornate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

In each of the embodiments the glycopeptide antibiotic may be bound to the surface or porous material through a non-covalent interaction or a covalent interaction.

In each of the methods of preventing the formation of a biofilm or preventing the colonization of dormant bacteria, a second antibiotic may be applied concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Prophylaxis

The invention is additionally generally directed to methods for providing prophylaxis of an infection caused by dormant bacteria in a subject, comprising administering to a subject having an infection caused by dormant bacteria an amount of a glycopeptide antibiotic sufficient to achieve prophylaxis of the infection, wherein the dormant bacteria is one or more of: (i) slow growing bacteria, (ii) stationary-phase bacteria and (iii) bacteria in biofilm form. The dormant bacteria may be contacted with the glycopeptide antibiotic in vitro, in vivo and/or ex vivo.

Preferably, the glycopeptide antibiotic is administered in the form of a pharmaceutical composition comprising the glycopeptide antibiotic and a pharmaceutically acceptable carrier or diluent. Preferably, the glycopeptide antibiotic is oritavancin, or a pharmaceutically acceptable salt, hydrate, or solvate thereof, or a mixture thereof.

In the preferred embodiments, the glycopeptide antibiotic is administered to the subject via intravenous administration or oral administration.

In each of the methods of providing prophylaxis of an infection caused by dormant bacteria, a second antibiotic may be administered concurrent with the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

Devices

The invention is also generally directed to a surface comprising a glycopeptide antibiotic in an amount sufficient to inhibit the growth of one or more of (i) slow growing bacteria, (ii) stationary-phase bacteria and (iii) bacteria in biofilm form. In one embodiment, the surface is an inert surface, such as the surface of an in-dwelling medical device. In preferred embodiments, the surface is coated by or impregnated with the glycopeptide antibiotic.

The invention is also generally directed to an in-dwelling medical device coated by or impregnated with a glycopeptide antibiotic in an amount sufficient to inhibit the growth of one or more of: (i) slow growing, (ii) stationary-phase and (iii) bacteria in a biofilm form. In a preferred embodiment, a surface of the in-dwelling medical device is coated by or impregnated with the glycopeptide antibiotic.

The invention is further generally directed to a porous material comprising a glycopeptide antibiotic in an amount sufficient to inhibit the growth of one or more of: (i) slow growing bacteria, (ii) stationary-phase bacteria and (iii) bacteria in biofilm form. In preferred embodiments, the surface is coated by or impregnated with the glycopeptide antibiotic.

The material comprising the surface or the porous material may be any material that can be used to form a surface or a porous material. In preferred embodiments, the material is selected from the group of consisting of polyethylene, polytetrafluoroethylene, polypropylene, polystyrene, polyacrylamide, polyacrylonitrile, poly(methyl methacrylate), polyamide, polyester, polyurethane, polycarbornate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

In each of the embodiments the glycopeptide antibiotic may be bound to the surface or porous material through a non-covalent interaction or a covalent interaction.

Preferably, the glycopeptide antibiotic is oritavancin, or a pharmaceutically acceptable salt, hydrate, or solvate thereof, or a mixture thereof.

The surface or porous material may further comprise a second antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

*Enterococcus faecalis* (VSE), VAN-resistant *E. faecalis* (VRE), and *Staph. epidermidis*.

The glycopeptide antibiotics for use in all aspects of the present invention include those of Formula I:

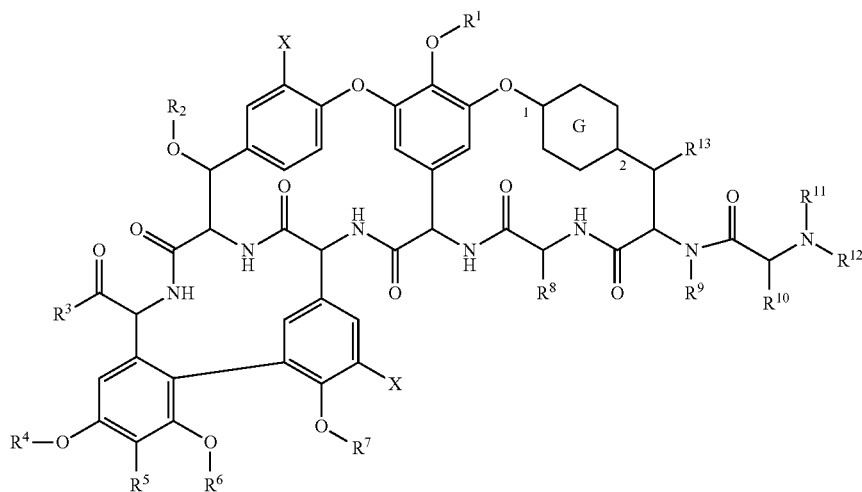

Formula I

Uses

The present invention also includes the use of a glycopeptide antibiotic in the manufacture of a medicament for inhibition, delay of formation, treatment, prophylaxis and/or prevention of one or more of: a (i) slow growing, (ii) stationary-phase or (iii) biofilm bacterial infection in a subject or on a surface. Preferably, said glycopeptide antibiotic is oritavancin, or pharmaceutically acceptable salt, hydrate, or solvate thereof, or a mixture thereof.

The uses of the present invention include the use of a second antibiotic in addition to the glycopeptide antibiotic. Suitable second antibiotics include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In each embodiment, the slow growing, stationary-phase or biofilm bacteria is any bacterial species that can exist in a slow growing or stationary-phase, or that can form a biofilm. In preferred embodiments, the bacteria is *Staphylococcus aureus, Staphylococcus epidermidis*, a vancomycin-susceptible enterococci, a vancomycin-resistant enterococci, a *Staphylococcus* species or a *Streptococcus* species. In further preferred embodiments, the bacteria is selected from the group consisting of vancomycin (VAN)-susceptible as well as pharmaceutically acceptable salts, hydrates and solvates thereof, and mixtures thereof, wherein:

$R^1$ is one of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$; or $R^1$ is a saccharide group optionally substituted with —$R^a$—Y—$R^b$—$(Z)_x$, $R^f$, —C(O)$R_f$, —$R^a$—$R^b$—$(Z)_x$, or —C(O)—$R^a$—Y—$R^b$—$(Z)_x$;

$R^2$ is hydrogen or a saccharide group optionally substituted with —$R^a$—Y—$R^b$—$(Z)_x$, $R^f$, —C(O)$R^f$, —$R^a$—$R^b$—$(Z)_x$, or —C(O)—$R^a$—Y—$R^b$—$(Z)_x$;

$R^3$ is ~$OR^c$, —$NR^cR^c$, —O—$R^a$—Y—$R^b$—$(Z)_x$, —$NR^c$—$R^a$—Y—$R^b$—$(Z)_x$, —$NR^cR^e$, or —O—$R^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, $R^f$, or —C(O)—$R^a$—Y—$R^b$—$(Z)_x$, or $R^4$ and $R^5$ can be joined, together with the atoms to which they are attached, to form a heterocyclic ring optionally substituted with —$NR^c$—$R^a$—Y—$R^b$—$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$—$(Z)_x$, —CH($R^c$)—$R^x$, and —CH($R^c$)—$NR^c$—$R^a$—C(O)—$R^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$R^a$—Y—$R^b$—$(Z)_x$, $R^f$, —C(O)$R^f$, or —C(O)—$R^a$—Y—$R^b$—$(Z)_x$, or $R^5$ and $R^6$ can be joined, together with the atoms to which they are attached, to form a heterocyclic ring optionally substituted with —$NR^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)$R^d$;

R[8] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —R$^a$—Y—R$^b$—(Z)$_x$;

R[9] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R[10] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R[8] and R[10] are joined to form —Ar$^1$—O—Ar$^2$—, where Ar$^1$ and Ar$^2$ are independently arylene or heteroarylene;

R[11] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R[10] and R[11] are joined, together with the carbon and nitrogen atoms to which they are attached, to form a heterocyclic ring;

R[12] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$, —R$^a$—Y—R$^b$—(Z)$_x$, and —C(O)—R$^b$—Y—R$^b$—(Z)$_x$, or R[11] and R[12] are joined, together with the nitrogen atom to which they are attached, to form a heterocyclic ring;

R[13] is selected from the group consisting of hydrogen or —OR[14];

R[14] is selected from hydrogen, —C(O)R$^d$ and a saccharide group;

R$^a$ is each independently selected from the group consisting of alkylene, substituted alkylene, alkenylene, substituted alkenylene, alkynylene and substituted alkynylene;

R$^b$ is each independently selected from the group consisting of a covalent bond, arylene, alkylene, substituted alkylene, alkenylene, substituted alkenylene, alkynylene and substituted alkynylene;

R$^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

R$^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is each a saccharide group;

R$^f$ is each independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

R$^x$ is an N-linked amino saccharide or an N-linked heterocycle;

X is each independently selected from hydrogen, fluoro, chloro, bromo or iodo;

Y is each independently selected from the group consisting of, —CH$_2$—, oxygen, sulfur, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(O)—, and —N(R$^c$)SO$_2$NR$^c$—;

Z is each independently selected from hydrogen, aryl, cycloalkyl, cycloalkenyl, heteroaryl, heterocyclic; or a saccharide;

x is 1 or 2; and

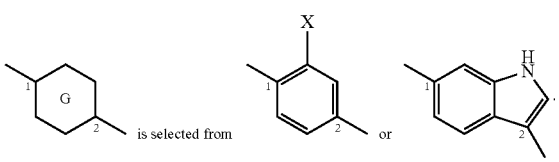

In particular, the glycopeptide antibiotics of Formula I include teicoplanin, dalbavancin and telavancin.

In an alternative embodiment, the glycopeptide antibiotics of Formula I exclude one or more of the following specific glycopeptide antibiotics: glycopeptide A35512 A, glycopeptide A35512 C, glycopeptide A35512 E, glycopeptide A35512 F, glycopeptide A35512 G, glycopeptide A35512H, glycopeptide A40926 A, glycopeptide A40926 B, glycopeptide A40926 PB, parvodicin B2, parvodicin C1, parvodicin C3, glycopeptide A41030, glycopeptide A42867, glycopeptide A477, glycopeptide A47934, glycopeptide A51568A, N-demethylvancomycin, glycopeptide A80407, glycopeptide A83850, glycopeptide A84575, glycopeptide AB65, glycopeptide AM374, actaplanin, glycopeptide A4696, actinoidin, ardacin, aricidin, glycopeptide AAD216, avoparcin, glycopeptide LL-AV290, azureomycin, balhimycin, balhimycin V, chloroorienticin, glycopeptide A82846B, glycopeptide LY264826, glycopeptide LY307599, chloroeremomycin, chloropeptin, chloropolysporin, complestatin, dalbavancin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosaminyl-vancomycin, eremomycin, galacardin, helvecardin, izupeptin, kibdelin, kistamicin, mannopeptin, methylbalhimycin, glycopeptide MM47761, glycopeptide MM47766, glycopeptide MM47767, glycopeptide MM49721, glycopeptide MM49727, glycopeptide MM55256, glycopeptide MM55260, glycopeptide MM55266, glycopeptide MM55268, glycopeptide MM55270, glycopeptide MM55272, glycopeptide MM56597, glycopeptide MM56598, nogabecin F, compound OA7653, orienticin, dechloroeremomycin, glycopeptide PA42867, glycopeptide PA45052, parvodicin, rhamnosyl-balhimycin, ristocetin, ristomycin, spontin, symnonicin, teichomycin, teicoplanin, teicoplanin A$_2$-1, teicoplanin A$_2$-2, teicoplanin A$_2$-3, teicoplanin A$_2$-4, teicoplanin A$_2$-5, teicoplanin R$_S$-1, teicoplanin R$_S$-2, teicoplanin R$_S$-3, teicoplanin R$_S$-4, telavancin, ureidobalhimycin, vancomycin, N-decylaminoethylvancomycin, N-(4-phenylbenzyl)vancomycin, N-(4-(4-chlorophenyl)benzyl)vancomycin and [ψ[CH$_2$NH]Tpg$^4$]vancomycin.

As a subset of Formula I, the glycopeptide antibiotics of the present invention also include those of Formula II:

17

Formula II

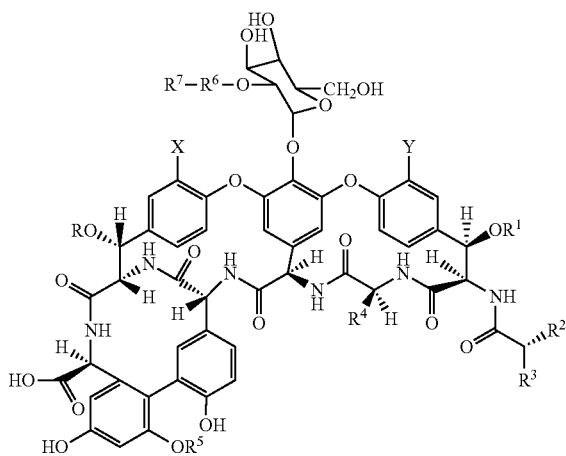

as well as pharmaceutically acceptable salts, hydrates and solvates thereof, and mixtures thereof, wherein:

X and Y are each independently hydrogen or chloro;

R is hydrogen, 4-epi-vancosaminyl, actinosaminyl, ristosaminyl, or a group of the formula —$R^a$—$R^{7a}$, wherein $R^a$ is 4-epi-vancosaminyl, actinosaminyl, or ristosaminyl, and $R^{7a}$, defined below, is attached to the amino group of $R^a$;

$R^1$ is hydrogen or mannose;

$R^2$ is —$NH_2$, —$NHCH_3$, —$N(CH_3)_2$, —$NHR^{7b}$, or —$N(CH_3)R^{7b}$, wherein $R^{7b}$ is defined below;

$R^3$ is —$CH_2CH(CH_3)_2$, [p-OH, m-Cl]phenyl, p-rhamnosyloxyphenyl, p-(rhamnosyl-galactosyloxy)-phenyl, [p-galactose-galactose]phenyl, p-(methoxyrhamnosyloxy)phenyl or p-(methoxyrhamnosyloxy)phenyl;

$R^4$ is —$CH_2(CO)NH_2$, benzyl, [p-OH]phenyl, or [p-OH, m-Cl]phenyl;

$R^5$ is hydrogen, or mannose;

$R^6$ is 4-epi-vancosaminyl, L-acosaminyl, L-ristosaminyl, or L-actinosaminyl;

$R^7$, as defined below, is attached to the amino group of $R^6$; and $R^7$, $R^{7a}$, and $R^{7b}$ are each independently selected from the group consisting of hydrogen, ($C_2$-$C_{16}$)alkenyl, ($C_2$-$C_{12}$) alkynyl, ($C_1$-$C_{12}$ alkyl)-$R^8$, ($C_1$-$C_{12}$ alkyl)-halo, ($C_2$-$C_6$ alkenyl)-$R^8$, ($C_2$-$C_6$ alkynyl)-$R^8$, and ($C_1$-$C_{12}$ alkyl)-O—$R^8$, provided that $R^7$, $R^{7a}$, and $R^{7b}$ are not all hydrogen, and $R^8$ is selected from the group consisting of:

a) multicyclic aryl unsubstituted or substituted with one or more substituents independently selected from the group consisting of:
(i) hydroxy,
(ii) halo,
(iii) nitro,
(iv) ($C_1$-$C_6$)alkyl,
(v) ($C_2$-$C_6$)alkenyl,
(vi) ($C_2$-$C_6$)alkynyl,
(vii) ($C_1$-$C_6$)alkoxy,
(viii) halo-($C_1$-$C_6$)alkyl,
(ix) halo-($C_1$-$C_6$)alkoxy,
(x) carbo-($C_1$-$C_6$)alkoxy,
(xi) carbobenzyloxy,

18

(xii) carbobenzyloxy substituted with ($C_1$-$C_6$)alkyl, ($C_1$-$C_6$)alkoxy, halo, or nitro,
(xiii) a group of the formula —$S(O)_{n'}$—$R^9$, wherein n' is 0-2 and $R^9$ is ($C_1$-$C_6$)alkyl, phenyl, or phenyl substituted with ($C_1$-$C_6$)alkyl, ($C_1$-$C_6$)alkoxy, halo, or nitro, and
(xiv) a group of the formula —$C(O)N(R^{10})_2$ wherein each $R^{10}$ substituent is independently hydrogen, ($C_1$-$C_6$)-alkyl, ($C_1$-$C_6$)-alkoxy, phenyl, or phenyl substituted with ($C_1$-$C_6$)-alkyl, ($C_1$-$C_6$)-alkoxy, halo, or nitro;

b) heteroaryl unsubstituted or substituted with one or more substituents independently selected from the group consisting of:
(i) halo,
(ii) ($C_1$-$C_6$)alkyl,
(iii) ($C_1$-$C_6$)alkoxy,
(iv) halo-($C_1$-$C_6$)alkyl,
(v) halo-($C_1$-$C_6$)alkoxy,
(vi) phenyl,
(vii) thiophenyl,
(viii) phenyl substituted with halo, ($C_1$-$C_6$)alkyl, ($C_2$-$C_6$) alkenyl, ($C_2$-$C_6$)alkynyl, ($C_1$-$C_6$)alkoxy, or nitro,
(ix) carbo-($C_1$-$C_6$)alkoxy,
(x) carbobenzyloxy,
(xi) carbobenzyloxy substituted with ($C_1$—$C_6$)alkyl, ($C_1$—$C_6$)alkoxy, halo, or nitro,
(xii) a group of the formula —$S(O)_{n'}$—$R^9$, as defined above,
(xiii) a group of the formula —$C(O)N(R^{10})_2$ as defined above, and
(xiv) thienyl;

c) a group of the formula:

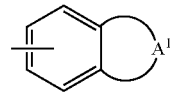

wherein $A^1$ is —$OC(A^2)_2$—$C(A^2)_2$—O—, —O—$C(A^2)_2$—O—, —$C(A^2)_2$—O—, or —$C(A^2)_2$—$C(A^2)_2$—$C(A^2)_2$-, and each $A^2$ substituent is independently selected from hydrogen, ($C_1$-$C_6$)-alkyl, ($C_1$-$C_6$)alkoxy, and ($C_4$-$C_{10}$) cyclo alkyl;

d) a group of the formula:

wherein p is from 1 to 5; and $R^{11}$ is independently selected from the group consisting of:
(i) hydrogen,
(ii) nitro,
(iii) hydroxy,
(iv) halo,
(v) ($C_1$-$C_8$)alkyl,
(vi) ($C_1$-$C_8$)alkoxy,
(vii) ($C_9$-$C_{12}$)alkyl,
(viii) ($C_2$-$C_9$)alkynyl, (ix) $(C_9-C_{12})$alkoxy,
(x) $(C_1-C_3)$alkoxy substituted with $(C_1-C_3)$alkoxy, hydroxy, halo$(C_1-C_3)$alkoxy, or $(C_1-C_4)$alkylthio,
(xi) $(C_2-C_5)$alkenyloxy,
(xii) $(C_2-C_{13})$alkynyloxy
(xiii) halo-$(C_1-C_6)$alkyl,
(xiv) halo-$(C_1-C_6)$alkoxy,
(xv) $(C_2-C_6)$alkylthio,
(xvi) $(C_2-C_{10})$alkanoyloxy,
(xvii) carboxy-$(C_2-C_4)$alkenyl,
(xviii) $(C_1-C_3)$alkylsulfonyloxy,
(xix) carboxy-$(C_1—C_3)$alkyl,
(xx) N-[di$(C_1-C_3)$-alkyl]amino-$(C_1-C_3)$alkoxy,
(xxi) cyano-$(C_1-C_6)$alkoxy, and
(xxii) diphenyl-$(C_1-C_6)$alkyl, with the proviso that when $R^{11}$ is $(C_1-C_8)$alkyl, $(C_1-C_8)$alkoxy, or halo, p must be greater or equal to 2, or when $R^7$ is $(C_1-C_3$ alkyl)-$R^8$ then $R^{11}$ is not hydrogen, $(C_1-C_8)$alkyl, $(C_1-C_8)$alkoxy, or halo;

e) a group of the formula:

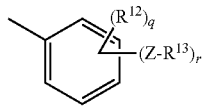

wherein q is 0 to 4; $R^{12}$ is independently selected from the group consisting of:
(i) halo,
(ii) nitro,
(iii) $(C_1-C_6)$alkyl,
(iv) $(C_1-C_6)$alkoxy,
(v) halo-$(C_1-C_6)$alkyl,
(vi) halo-$(C_1-C_6)$alkoxy,
(vii) hydroxy, and
(vii) $(C_1-C_6)$thioalkyl, r is 1 to 5; provided that the sum of q and r is no greater than 5;

Z is selected from the group consisting of:
(i) a single bond,
(ii) divalent $(C_1-C_6)$alkyl unsubstituted or substituted with hydroxy, $(C_1-C_6)$alkyl, or $(C_1-C_6)$alkoxy,
(iii) divalent $(C_2-C_6)$alkenyl,
(iv) divalent $(C_2-C_6)$alkynyl, and
(v) a group of the formula —$(C(R^{14})_2)_s$—$R^{15}$— or —$R^{15}$—$(C(R^{14})_2)_s$—, wherein s is 0-6; wherein each $R^{14}$ substituent is independently selected from hydrogen, $(C_1-C_6)$-alkyl, or $(C_4-C_{10})$cycloalkyl; and $R^{15}$ is selected from —O—, —S—, —SO—, —SO$_2$—, —SO$_2$—O—, —C(O)—, —OC(O)—, —C(O)O—, —NH—, —N($C_1-C_6$ alkyl)-, and —C(O)NH—, —NHC(O)—, N=N;

$R^{13}$ is independently selected from the group consisting of:
(i) $(C_4-C_{10})$heterocyclyl,
(ii) heteroaryl,
(iii) $(C_4-C_{10})$cycloalkyl unsubstituted or substituted with $(C_1-C_6)$alkyl, and
(iv) phenyl unsubstituted or substituted with 1 to 5 substituents independently selected from: halo, hydroxy, nitro, $(C_1-C_{10})$alkyl, $(C_1-C_{10})$alkoxy, halo-$(C_1-C_3)$alkoxy, halo-$(C_1-C_3)$alkyl, $(C_1-C_3)$alkoxyphenyl, phenyl, phenyl-$(C_1-C_3)$alkyl, $(C_1-C_6)$alkoxyphenyl, phenyl-$(C_2-C_3)$alkynyl, and $(C_1-C_6)$alkylphenyl;

f) $(C_4-C_{10})$cycloalkyl unsubstituted or substituted with one or more substituents independently selected from the group consisting of:
(i) $(C_1-C_6)$alkyl,
(ii) $(C_1-C_6)$alkoxy,
(iii) $(C_2-C_6)$alkenyl,
(iv) $(C_2-C_6)$alkynyl,
(v) $(C_4-C_{10})$cycloalkyl,
(vi) phenyl,
(vii) phenylthio,
(viii) phenyl substituted by nitro, halo, $(C_1-C_6)$alkanoyloxy, or carbocycloalkoxy, and
(ix) a group represented by the formula —Z—$R^{13}$ wherein Z and $R^{13}$ are as defined above; and g) a group of the formula:

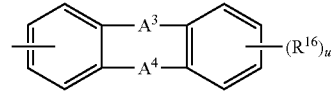

wherein $A^3$ and $A^4$ are each independently selected from
(i) a bond,
(ii) —O—,
(iii) —S(O)$_t$—, wherein t is 0 to 2,
(iv) —C($R^{17}$)$_2$—, wherein each $R^{17}$ substituent is independently selected from hydrogen, $(C_1-C_6)$alkyl, hydroxy, $(C_1-C_6)$alkyl, $(C_1-C_6)$alkoxy, or both $R^{17}$ substituents taken together are O,
(v) —N($R^{18}$)$_2$—, wherein each $R^{18}$ substituent is independently selected from hydrogen; $(C_1-C_6)$alkyl; $(C_2-C_6)$alkenyl; $(C_2-C_6)$alkynyl; $(C_4-C_{10})$cycloalkyl; phenyl; phenyl substituted by nitro, halo, $(C_1-C_6)$alkanoyloxy; or both $R^{18}$ substituents taken together are $(C_4-C_{10})$cycloalkyl;

$R^{16}$ is $R^{12}$ or $R^{13}$ as defined above; and u is 0-4.

The glycopeptide antibiotics of the present invention include each of those disclosed in U.S. Pat. No. 5,840,684, incorporated herein by reference in its entirety.

Oritavancin (also termed N-(4-(4-chlorophenyl)benzyl) A82846B and LY333328) has the following Formula III:

Formula III

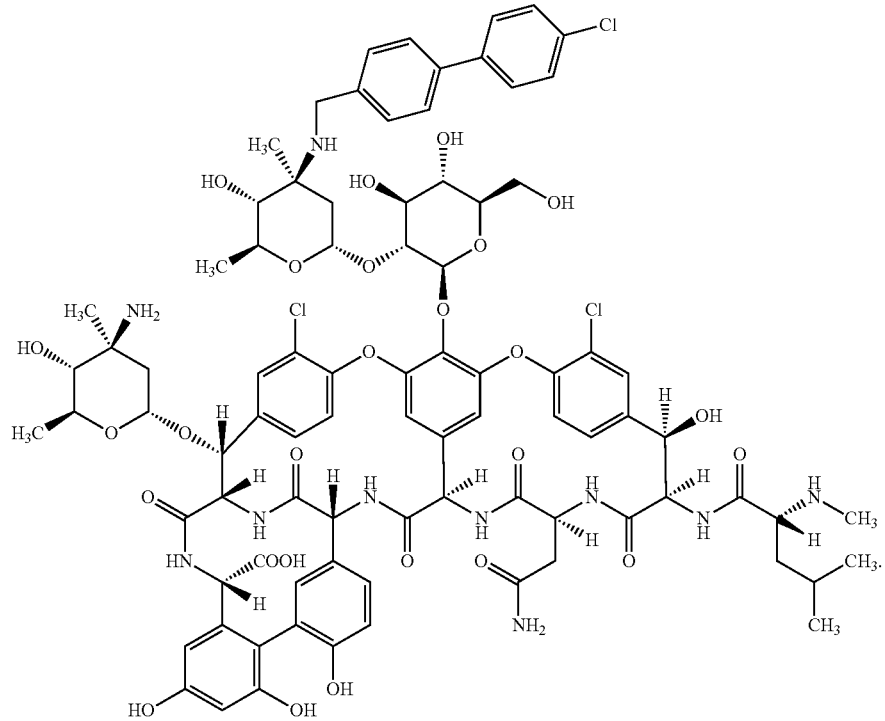

Other specific glycopeptide antibiotics that may be used in the methods disclosed herein include: glycopeptide A35512 A, glycopeptide A35512 C, glycopeptide A35512 E, glycopeptide A35512 F, glycopeptide A35512 G, glycopeptide A35512H, glycopeptide A40926 A, glycopeptide A40926 B, glycopeptide A40926 PB, parvodicin B2, parvodicin C1, parvodicin C3, glycopeptide A41030, glycopeptide A42867, glycopeptide A477, glycopeptide A47934, glycopeptide A51568A, N-demethylvancomycin, glycopeptide A80407, glycopeptide A83850, glycopeptide A84575, glycopeptide AB65, glycopeptide AM374, actaplanin, glycopeptide A4696, actinoidin, ardacin, aricidin, glycopeptide AAD216, avoparcin, glycopeptide LL-AV290, azureomycin, balhimycin, balhimycin V, chloroorienticin, glycopeptide A82846B, glycopeptide LY264826, glycopeptide LY307599, chloroeremomycin, chloropeptin, chloropolysporin, complestatin, dalbavancin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosaminyl-vancomycin, eremomycin, galacardin, helvecardin, izupeptin, kibdelin, kistamicin, mannopeptin, methylbalhimycin, glycopeptide MM47761, glycopeptide MM47766, glycopeptide MM47767, glycopeptide MM49721, glycopeptide MM49727, glycopeptide MM55256, glycopeptide MM55260, glycopeptide MM55266, glycopeptide MM55268, glycopeptide MM55270, glycopeptide MM55272, glycopeptide MM56597, glycopeptide MM56598, nogabecin F, compound OA7653, orienticin, dechloroeremomycin, glycopeptide PA42867, glycopeptide PA45052, parvodicin, rhamnosyl-balhimycin, ristocetin, ristomycin, spontin, symnonicin, teichomycin, teicoplanin, teicoplanin $A_2$-1, teicoplanin $A_2$-2, teicoplanin $A_2$-3, teicoplanin $A_2$-4, teicoplanin $A_2$-5, teicoplanin $R_S$-1, teicoplanin $R_S$-2, teicoplanin $R_S$-3, teicoplanin $R_S$-4, telavancin, ureido-balhimycin, vancomycin, N-decylaminoethylvancomycin, N-(4-phenylbenzyl)vancomycin, N-(4-(4-chlorophenyl)benzyl)vancomycin and [ψ[$CH_2NH$]Tpg$^4$]vancomycin.

The alkyl substituents recited herein denote substituted or unsubstituted, straight or branched chain hydrocarbons of the length specified. The term "alkenyl" refers to a substituted or unsubstituted, straight or branched alkenyl chain of the length specified herein. The term "alkynyl" refers to a substituted or unsubstituted, straight or branched alkynyl chain of the length specified herein.

The alkoxy substituents recited herein represent an alkyl group attached through an oxygen bridge. The term "alkenoxy" represents an alkenyl chain of the specified length attached to an oxygen atom.

The term "multicyclic aryl" means a stable, saturated or unsaturated, substituted or unsubstituted, 9 to 10 membered organic fused bicyclic ring; a stable, saturated or unsaturated, substituted or unsubstituted 12 to 14 membered organic fused tricyclic ring; or a stable, saturated or unsaturated, substituted or unsubstituted 14 to 16 membered organic fused tetracyclic ring. The bicyclic ring may have 0 to 4 substituents, the tricyclic ring may have 0 to 6 substituents, and the tetracyclic ring may have 0 to 8 substituents. Typical multi-cyclic aryls include fluorenyl, napthyl, anthranyl, phenanthranyl, biphenylene and pyrenyl.

The term "heteroaryl" represents a stable, saturated or unsaturated, substituted or unsubstituted, 4 to 7 membered organic monocyclic ring having a hetero atom selected from S, O, and N; a stable, saturated or unsaturated, substituted or unsubstituted, 9 to 10 membered organic fused bicyclic ring having 1 to 2 hetero atoms selected from S, O, and N; or a stable, saturated or unsaturated, substituted or unsubstituted, 12 to 14 membered organic fused tricyclic ring having a hetero atom selected from S, O, and N. The nitrogen and sulfur atoms of these rings are optionally oxidized, and the nitrogen hetero atoms are optionally quarternized. The monocyclic ring may have 0 to 5 substituents. The bicyclic ring may have 0 to 7 substituents, and the tricyclic ring may have 0 to 9 substituents. Typical heteroaryls include quinolyl, piperidyl, thienyl, piperonyl, oxafluorenyl, pyridyl and benzothienyl and the like.

The term "$(C_4-C_{10})$cycloalkyl" embraces substituents having from four to ten carbon atoms, such as cyclobutyl, cyclopentyl, cyclohexyl, and cycloheptyl which may be unsubstituted or substituted with substituents such as alkyl and phenyl. This term also embraces $C_5$ to $C_{10}$ cycloalkenyl groups such as cyclopentenyl and cyclohexenyl. The term "$(C_4-C_{10})$cycloalkyl" also embraces bicyclic and tricyclic cycloalkyls such as bicyclopentyl, bicylohexyl, bicycloheptyl, and adamantyl.

The term "alkanoyloxy" represents an alkanoyl group attached through an oxygen bridge. These substituents may be substituted or unsubstituted, straight, or branched chains of the specified length.

The term "cyano-$(C_1-C_6)$ alkoxy" represents a substituted or unsubstituted, straight or branched alkoxy chain having from one to six carbon atoms with a cyano moiety attached to it.

The term "divalent $(C_1-C_6)$ alkyl" represents an unsubstituted or substituted, straight or branched divalent alkyl chain having from one to six carbon atoms. Typical divalent $(C_1-C_6)$ alkyl groups include methylene, ethylene, propylene, isopropylene, butylene, isobutylene, secbutylene, t-butylene, pentylene, neo-pentylene, and hexylene. Such divalent $(C_1-C_6)$ alkyl groups may be substituted with substituents such as alkyl, alkoxy, and hydroxy.

The term "divalent $(C_2-C_6)$alkenyl" represents a straight or branched divalent alkenyl chain having from two to six carbon atoms. Typical divalent $(C_2-C_6)$ alkenyl include ethenyl, 1-propenyl, 2-propenyl, 1-butenyl, 2-butenyl and the like.

The term "divalent $(C_2-C_6)$ alkynyl" represents a straight or branched divalent alkynyl chain having from two to six carbon atoms. Typical divalent $(C_2-C_6)$ alkynyl include ethynylene, 1-propynylene, 2-propynylene, 1-butynylene, 2-butynylene and the like.

The term "halo" represents chloro, fluoro, bromo or iodo.

The term "halo-$(C_1-C_6)$alkyl" represents a straight or branched alkyl chain having from one to six carbon atoms with from 0 to 3 halogen atoms attached to each carbon.

Typical halo-$(C_1-C_6)$ alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

The term "halo-$(C_1-C_6)$alkoxy" represents a straight or branched alkoxy chain having from one to six carbon atoms with from 0 to 3 halogen atoms attached to each carbon.

Typical halo-$(C_1-C_6)$ alkoxy groups include chloromethoxy, 2-bromoethoxy, 1-chloroisopropoxy, 3-fluoropropoxy, 2,3-dibromobutoxy, 3-chloroisobutoxy, iodo-t-butoxy, trifluoromethoxy, and the like.

The term "heterocyclyl" embraces saturated groups having three to ten ring members and which heterocyclic ring contains a hetero atom selected from oxygen, sulfur and nitrogen, examples of which are piperazinyl, morpholino, piperdyl, methylpiperdyl, azetidinyl, and aziridinyl.

The glycopeptide antibiotics of the present invention, including oritavancin, may be used per se or in the form of a pharmaceutically acceptable salt, hydrate, solvate, or mixtures thereof. The term "pharmaceutically acceptable salt" refers to non-toxic acid addition salts derived from inorganic and organic acids.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of the glycopeptide antibiotics, including oritavancin and analogs thereof, may be found, for example, in U.S. Pat. No. 5,840,684, incorporated herein by reference in its entirety.

As used herein, a "subject" refers to an animal, such as a mammal, preferably a human. The subject may have a slow growing, stationary-phase or biofilm bacterial infection, may be at risk for developing a slow growing, stationary-phase or biofilm bacterial infection, or may be at greater risk than the general population for developing a slow growing, stationary-phase or biofilm bacterial infection. Examples of subjects having a higher risk for developing a slow growing, stationary-phase or biofilm bacterial infection include those subjects having an in-dwelling medical device.

The methods of the present invention include those performed in vivo, in vitro or ex vivo. The in vitro methods are exemplified by, but not limited to, methods performed in a laboratory setting, such as in a cell culture, as well as methods performed on inert objects, such as laboratory or hospital equipment or in-dwelling medical devices, and on surfaces such as countertops and bench tops. The ex vivo methods are exemplified by, but not limited to, methods performed on the surface of the human body, such as on the skin in general. The in vivo methods are exemplified by, but not limited to, methods of treatment, prevention, propylaxis, delay, or inhibition of infections on or within an animal body, such as on or in an opening into the body, whether naturally occurring or medically created, such as for the placement of an in-dwelling medical device, or a wound in the skin, on or in a tissue, on or in organ, on or in system, or in a fluid of the body of a subject.

The methods of the present invention include both those where one or more glycopeptide antibiotics are used, as well as those where pharmaceutical compositions comprising one or more glycopeptide antibiotics are used. The pharmaceutical compositions of the present invention comprise one or more glycopeptide antibiotics, and one or more of a carrier, diluent and excipient. Suitable carriers, diluents and excipients are well known to those skilled in the art and include saline, buffered saline, dextrose (e.g., 5% dextrose in water), water, glycerol, ethanol, propylene glycol, polysorbate 80 (Tween-80™), 0.002% polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholids, polymer matrices, biocompatible polymers, liposphere, vesicles, particles, and liposomes. The terms specifically exclude cell culture medium.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

The pharmaceutical compositions and glycopeptide antibiotics of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vasoconstrictors for prolongation and agents that increase tissue permeability), and combinations thereof.

Parenteral formulations using hydrophobic carriers include, for example, fat emulsions and formulations containing lipids, liposphere, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of glycopeptide antibiotics can be a ready-to-use solution of the glycopeptide antibiotic in a suitable carrier in sterile, hermetically sealed ampoules or in sterile pre-loaded syringes. The suitable carrier optionally comprises any of the above-mentioned excipients.

Alternatively, the unit dosage of the glycopeptide antibiotics of the present invention can be in a concentrated liquid, powder or granular form for ex tempore reconstitution in the appropriate pharmaceutically acceptable carrier at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose or Ringer's™ solution.

In intramuscular preparations, a sterile formulation of the pharmaceutical compositions of the present invention can be dissolved and administered in a pharmaceutical diluent such as Water-for-Injection (WFI), physiological saline or 5% dextrose. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to the glycopeptide antibiotics, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

In a particular oral formulation, the glycopeptide antibiotics of the present invention may be in the form of a capsule containing the glycopeptide antibiotic, gelatin, iron oxide, polyethylene glycol, titanium dioxide, and one or more other inactive ingredients. Suitable amounts of the glycopeptide antibiotic in the capsule may range from 10 to 1000 mg, with preferred amounts including 100, 125, 150, 175, 200, 225, 250, 275, 300, 350, 400, 450 or 500 mg of the glycopeptide antibiotic.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

The term "dose", "unit dose", "unit dosage", or "effective dose" refers to physically discrete units that contain a predetermined quantity of active ingredient calculated to produce a desired therapeutic effect.

Each of (i) an amount sufficient to inhibit the growth of a dormant bacteria, (ii) a therapeutically effective amount of the glycopeptide antibiotic, (iii) an amount of a glycopeptide antibiotic sufficient to prevent an infection, (iv) an amount of a glycopeptide antibiotic sufficient to prevent biofilm formation, and (v) an amount of a glycopeptide antibiotic sufficient to achieve prophylaxis of an infection, will vary depending upon the physical characteristics of the patient, the severity of the patient's symptoms, the formulation and the means used to administer the drug, the location of the bacteria or infection, and the identity of the bacteria. The specific dose for a given patient is usually set by the judgment of the attending physician. However, in each case the amount of the glycopeptide antibiotic administered will typically be between about 0.5 mg/kg body weight to about 500 mg/kg body weight, preferably from about 1 to about 100 mg/kg, more preferably from about 3 to about 50 mg/kg, regardless of the formulation. In equally preferred embodiments, the amount of the glycopeptide antibiotic administered is about 3, 5, 10, 15, 20, 25, 30, 35, 40, 45 or 50 mg/kg body weight, regardless of the formulation. In some situations, a dose less than about 0.5 mg/kg body weight may be effective.

Each of (i) an amount of glycopeptide antibiotic sufficient to inhibit the formation of a biofilm on a surface, (ii) an amount of glycopeptide antibiotic sufficient to delay the formation of a biofilm on a surface, (iii) an amount of a glycopeptide antibiotic sufficient to prevent colonization of a surface by a dormant bacteria, and (iv) an amount of a glycopeptide antibiotic sufficient to prevent colonization of a porous material by a dormant bacteria, will varying depending on the physical properties of the surface or porous material to which the glycopeptide antibiotic is applied, the location of the surface or porous material, the formulation and the means used to apply the glycopeptide antibiotic, the location of the biofilm or dormant bacteria, and the identity of the dormant bacteria or the bacteria forming the biofilm. However, the concentration of glycopeptide antibiotic sufficient to inhibit or delay the formation or colonization of a dormant bacteria or a biofilm on a surface or porous material will typically be between about 10 ug/ml to about 500 mg/ml of a glycopeptide antibiotic. In particular embodiments, more specific ranges of concentrations of the glycopeptide antibiotic may be used, including: about 10 ug/ml to about 1 mg/ml, about 1 mg/ml to about 100 mg/ml, about 10 mg/ml to about 500 mg/ml, about 50 mg/ml to about 200 mg/ml, about 10 mg/ml to about 100 mg/ml, about 100 mg/ml to about 500 mg/ml. In particular embodiments, specific concentrations of the glycopeptide antibiotic may be used, including: about 10 ug/ml, about 50 ug/ml, about 100 ug/ml, about 250 ug/ml, about 500 ug/ml, about 750 ug/ml, about 1 mg/ml, about 5 mg/ml, about 10 mg/ml, about 15 mg/ml, about 20 mg/ml, about 25 mg/ml, about 30 mg/ml, about 40 mg/ml, about 50 mg/ml, about 75 mg/ml, about 100 mg/ml, about 250 mg/ml, about 500 mg/ml, about 600 mg/ml, about 750 mg/ml, and about 900 mg/ml.

Suitable frequencies of administration or application may vary based on whether administration or application is for the purposes of inhibition, delay of formation, treatment, prophylaxis or prevention. Administration frequencies for the treatment of a subject having a slow growing, stationary-phase or biofilm bacterial infection, or for use in delay of formation, prophylaxis or prevention of such an infection, include 4 times per day, 3 times per day, 2 times per day or once daily, every other day, every third day, every fourth day, every fifth day, every sixth day, once weekly, every eight days, every nine days, every ten days, bi-weekly, monthly and bi-monthly. Administration or application may also be limited to a single administration or application.

In further embodiments, one or more additional (second) antibacterial agents may be used in combination with the glycopeptide antibiotics in each of the methods of inhibition, treatment, prevention and prophylaxis of the present invention. For example, the methods of inhibiting the growth of dormant bacteria in a subject or the methods of treating an infection caused by dormant bacteria in a subject may include the concurrent administration of a second antibacterial agent with the glycopeptide antibiotic. The skilled artisan will understand that concurrent administration includes administration of the glycopeptide antibiotic and second antibacterial agent at the same time or serially but during the same course of administration. The second antibiotic may be selected from the group consisting of fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

As used herein, the terms "inhibit", "inhibiting" and "inhibition" have their ordinary and customary meanings, and include inhibiting the growth or cell divisional of a slow growing, stationary-phase or biofilm bacteria, as well as killing such bacteria. Thus, the bacteriostatic and bacteriocidal activities of the glycopeptides of the present invention are forms of inhibition. Such inhibition is an inhibition of about 1% to about 100% of the growth of the bacteria versus the growth of bacteria not contacted by the glycopeptide antibiotics of the present invention. Preferably, the inhibition is an inhibition of about 100%, 99%, 98%, 97%, 96%, 95%, 90%, 80%, 70%, 60%, 50%, 40%, 30%, 20%, 10%, 5% or 1% of the growth of the bacteria versus the growth of bacteria not contacted by the glycopeptide antibiotics of the present invention.

As used herein, the terms "delaying", "delay of formation", and "delaying of formation" have their ordinary and customary meanings, and are generally directed to increasing the period of time prior to the formation of biofilm, or a slow growing or stationary-phase bacterial infection. The delay may be, for example, about 12 hours, about 18 hours, about 24 hours, about 36 hours, about 48 hours, about 60 hours, about 72 hours, about 84 hours, about 96 hours, about 5, 6, 7, 8, 9, or 10 or more days.

As used herein, the terms "treating" and "treatment" have their ordinary and customary meanings, and include one or more of, ameliorating a symptom of a slow growing, stationary-phase or biofilm bacterial infection in a subject, blocking or ameliorating a recurrence of a symptom of a slow growing, stationary-phase or biofilm bacterial infection in a subject, decreasing in severity and/or frequency a symptom of a slow growing, stationary-phase or biofilm bacterial infection in a subject, and stasis, decreasing, or inhibiting growth of a slow growing, stationary-phase or biofilm bacterial infection in a subject. Treatment means ameliorating, blocking, reducing, decreasing or inhibiting by about 1% to about 100% versus a subject to which a pharmaceutical composition or glycopeptide antibiotic of the present invention has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition or glycopeptide antibiotic of the present invention has not been administered.

As used herein, the terms "preventing" and "prevention" have their ordinary and customary meanings, and include one or more of preventing colonization of a slow growing, stationary-phase or biofilm bacteria in a subject, or on a surface or on a porous material, preventing an increase in the growth of a population of a slow growing, stationary-phase or biofilm bacteria in a subject, or on a surface or on a porous material, preventing development of a disease caused by a slow growing, stationary-phase or biofilm bacteria in a subject, and preventing symptoms of a disease caused by a slow growing, stationary-phase or biofilm bacteria in a subject. As used herein, the prevention lasts at least about 0.5, 1, 2, 3, 4, 5, 6, 7, 10, 12, 15, 20, 25, 30, 35 40 or more days after administration or application of a pharmaceutical composition or glycopeptide antibiotic of the present invention.

As used herein, "prophylaxis" includes inhibiting the development of a productive or progressive infection by a slow growing, stationary-phase or biofilm bacteria in a subject, where the prophylaxis lasts at least about 0.5, 1, 2, 3, 4, 5, 6, 7, 10, 12, 15, 20, 25, 30, 35, 40 or more days after administration of a pharmaceutical composition or glycopeptide antibiotic of the present invention. Inhibition against development of a productive or progressive infection by a slow growing, stationary-phase or biofilm bacteria means that the severity of a slow growing, stationary-phase or biofilm bacteria infection in a subject is reduced by about 1% to about 100% versus a subject to which a pharmaceutical composition or glycopeptide antibiotic of the present invention has not been administered. Preferably, the reduction in severity is about a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of a slow growing, stationary-phase or biofilm bacteria present in a subject, the length of time that a slow growing, stationary-phase or biofilm bacteria can be detected in a subject, and/or the severity of a symptom of a slow growing, stationary-phase or biofilm bacterial infection, among other factors.

Each of the methods of inhibition, delay of formation, treatment, prophylaxis and prevention of a slow growing, stationary-phase or biofilm bacteria of the present invention may be used as a method for achieving a systemic and/or local effect against relevant bacteria shortly before an invasive medical treatment, such as surgery or insertion of an in-dwelling device (e.g. joint replacement (hip, knee, shoulder, etc.)). Treatment may be continued after invasive medical treatment, such as post-operatively or during the in-body time of the device.

In each instance, the pharmaceutical composition or glycopeptide antibiotic of the present invention may be administered once, twice, thrice or more, from 1, 2, 3, 4, 5, 6, 7 days or more, to 10, 9, 8, 7, 6, 5, 4, 3, 2, or 1 hour or less before surgery for permitting an advisable systemic or local presence of the pharmaceutical composition or glycopeptide antibiotic. The pharmaceutical composition or glycopeptide antibiotic may be administered after the invasive medical treatment for a period of time, such as 1, 2, 3, 4, 5 or 6 days, 1, 2, 3 or more weeks, or for the entire time in which the device is present in the body.

As used herein, the term "bi-weekly" refers to a frequency of every 13-15 days, the term "monthly" refers a frequency of every 28-31 days and "bi-monthly" refers a frequency of every 58-62 days.

As used herein, the term "contacting" is meant to broadly refer to bringing a bacterial cell and a molecule of a glycopeptide antibiotic of the present invention into sufficient proximity that the glycopeptide antibiotic can exert an effect on the bacterial cell. The glycopeptide antibiotic may be transported to the location of the bacterial cell, or the glycopeptide antibiotic may be situated in a location to which the bacterial cell travels or is brought into contact. The skilled artisan will understand that the term "contacting" includes physical interaction between a glycopeptide antibiotic and a bacterial cell, as well as interactions that do not require physical interaction.

The present invention further encompasses surfaces coated by a glycopeptide antibiotic of the invention, or impregnated with a glycopeptide antibiotic of the present invention. Such surfaces include any that may come into contact with a slow growing, stationary-phase or biofilm bacteria. In one embodiment, such surfaces include any surface made of an inert material, although surfaces of a living animal are encompassed within the scope of the invention, including the surface of a counter or bench top, the surface of a piece of medical or laboratory equipment or a tool, and the surface of in-dwelling medical device. In a particular embodiment, such surfaces include those of an in-dwelling medical device, such as surgical implants, orthopedic devices, prosthetic devices and catheters, i.e., devices that are introduced to the body of an individual and remain in position for an extended time. Such devices include, but are not limited to, artificial joints, artificial hearts and implants; valves, such as heart valves; pacemakers; vascular grafts; catheters, such as vascular, urinary and continuous ambulatory peritoneal dialysis (CAPD) catheters; shunts, such as cerebrospinal fluid shunts; hoses and tubing; plates; bolts; valves; patches; wound closures, including sutures and staples; dressings; and bone cement.

The present invention also encompasses porous materials to which the glycopeptide antibiotics of the present invention are applied, coated or impregnated.

The material comprising the surface or the porous material may be any material that can be used to form a surface or a porous material. In preferred embodiments, the material is selected from the group of consisting of polyethylene, polytetrafluoroethylene, polypropylene, polystyrene, polyacrylamide, polyacrylonitrile, poly(methyl methacrylate), polyamide, polyester, polyurethane, polycarbornate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

In each of the embodiments the glycopeptide antibiotic may be bound to the surface or porous material through a non-covalent interaction or a covalent interaction.

According to one embodiment, the surface or porous material is coated by a solution, such as through bathing or spraying, containing a concentration of about 10 ug/ml to about 500 mg/ml of a glycopeptide antibiotic of the present invention. In particular embodiments, more specific ranges of concentrations of the glycopeptide antibiotic may be used, including: about 10 ug/ml to about 1 mg/ml, about 1 mg/ml to about 100 mg/ml, about 10 mg/ml to about 500 mg/ml, about 50 mg/ml to about 200 mg/ml, about 10 mg/ml to about 100 mg/ml, about 100 mg/ml to about 500 mg/ml. In particular embodiments, specific concentrations of the glycopeptide antibiotic may be used, including: about 10 ug/ml, about 50 ug/ml, about 100 ug/ml, about 250 ug/ml, about 500 ug/ml, about 750 ug/ml, about 1 mg/ml, about 5 mg/ml, about 10 mg/ml, about 15 mg/ml, about 20 mg/ml, about 25 mg/ml, about 30 mg/ml, about 40 mg/ml, about 50 mg/ml, about 75 mg/ml, about 100 mg/ml, about 250 mg/ml, about 500 mg/ml, about 600 mg/ml, about 750 mg/ml, and about 900 mg/ml. When being applied to an in-dwelling medical device, the surface may be coated by the solution containing a glycopeptide antibiotic before its insertion in the body.

According to a further embodiment, the surface or porous material may be constructed whereby a glycopeptide antibiotic of the present invention is included in the material forming the surface or porous material. Thus, such a surface or porous material will be impregnated with a glycopeptide antibiotic of the present invention. For example, a glycopeptide antibiotic of the present invention may be included at an appropriate step during the manufacture of a surface or porous material to which a slow growing, stationary-phase or biofilm bacteria will come into contact, such as an in-dwelling medical device.

For surfaces or porous materials coated with a glycopeptide antibiotic of the invention, or impregnated with a glycopeptide antibiotic of the present invention, the glycopeptide antibiotic may form a covalent and non-covalent association with a component of the surface or porous material. Covalent associations include direct chemical bonds to a component of the surface, or an association through a linker, whether cleavable or non-cleavable, attaching the glycopeptide antibiotic to a component of the surface.

In further embodiments of the invention, one or more additional (second) antibacterial agents may be used in combination with the glycopeptide antibiotic of the present invention, and thus be included in the solution which is applied to a surface or a porous material, or in the material that is used in the preparation of a surface or porous material and that is impregnated with a glycopeptide antibiotic. The second antibiotic may be selected from the group consisting of fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, aminocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

The invention is also generally directed to an in-dwelling medical device coated by or impregnated with a glycopeptide antibiotic in an amount sufficient to inhibit the growth of a (i) slow growing, (ii) stationary-phase or (iii) biofilm bacteria. As described above, in-dwelling medical devices include surgical implants, orthopedic devices, prosthetic devices and catheters, i.e., devices that are introduced to the body of an individual and remain in position for an extended time. Such devices include, but are not limited to, artificial joints, artificial hearts and implants; valves, such as heart valves; pacemakers; vascular grafts; catheters, such as vascular, urinary and continuous ambulatory peritoneal dialysis (CAPD) catheters; shunts, such as cerebrospinal fluid shunts; hoses and tubing; plates; bolts; valves; patches; wound closures, including sutures and staples; dressings; and bone cement.

According to one embodiment, the in-dwelling medical device is coated by a solution, such as through bathing or spraying, containing a concentration of about 10 ug/ml to about 500 mg/ml of a glycopeptide antibiotic of the present invention. In particular embodiments, more specific ranges of concentrations of the glycopeptide antibiotic may be used, including: about 10 ug/ml to about 1 mg/ml, about 1 mg/ml to about 10 mg/ml, about 10 mg/ml to about 500 mg/ml, about 50 mg/ml to about 200 mg/ml, about 10 mg/ml to about 100 mg/ml, about 100 mg/ml to about 500 mg/ml. In particular embodiments, specific concentrations of the glycopeptide antibiotic may be used, including: about 10 ug/ml, about 50 ug/ml, about 100 ug/ml, about 250 ug/ml, about 500 ug/ml, about 750 ug/ml, about 1 mg/ml, about 5 mg/ml, about 10 mg/ml, about 15 mg/ml, about 20 mg/ml, about 25 mg/ml, about 30 mg/ml, about 40 mg/ml, about 50 mg/ml, about 75 mg/ml, about 100 mg/ml, about 250 mg/ml, about 500 mg/ml, about 600 mg/ml, about 750 mg/ml, and about 900 mg/ml. The in-dwelling medical device may be coated by the solution containing a glycopeptide antibiotic of the present invention before its insertion in the body.

According to a further embodiment, a component of the in-dwelling medical device may be constructed whereby a glycopeptide antibiotic of the present invention is included in the material forming the component. Thus, such a component will be impregnated with a glycopeptide antibiotic of the present invention. For example, a glycopeptide antibiotic of the present invention may be included at an appropriate step during the manufacture of a component to which a slow growing, stationary-phase or biofilm bacteria will come into contact.

For in-dwelling medical device coated with a glycopeptide antibiotic of the invention, or impregnated with a glycopeptide antibiotic of the present invention, the glycopeptide antibiotic may form a covalent and non-covalent association with a material forming a component of the in-dwelling medical device or a material forming the entire in-dwelling medical device. Covalent associations include direct chemical bonds to a material, or an association through a linker, whether cleavable or non-cleavable, attaching the glycopeptide antibiotic to the material.

In further embodiments of the invention, the one or more additional (second) antibacterial agents discussed herein may be used in combination with the glycopeptide antibiotic of the present invention, and thus be included in the solution which is applied to an in-dwelling medical device or that is used in the preparation of a material used in forming the in-dwelling medical device.

In each of the methods of the present invention, the glycopeptide antibiotics may be used in the inhibition, delay of formation, treatment, prevention and/or prophylaxis of an infection caused by dormant bacteria. As used herein, dormant bacteria are any bacteria that are resistant to the effects of an antibacterial agent due to the particular growth stage or formation of the bacteria. Dormant bacteria include those bacteria that are not actively undergoing DNA synthesis or cell division. As an example, dormant bacteria include those species resistant to the effects of an antibacterial agent that targets a function or property of dividing cells. Particular examples of dormant bacteria include bacteria that are slow growing or in a stationary-phase, as well as bacteria that have formed a biofilm. In preferred embodiments, the bacteria is *Staphylococcus aureus, Staphylococcus epidermidis*, a vancomycin-susceptible enterococci, a vancomycin-resistant enterococci, *Staphylococcus* species or a *Streptococcus* species. In further preferred embodiments, the bacteria is selected from the group consisting of vancomycin (VAN)-susceptible *Enterococcus faecalis* (VSE), VAN-resistant *E. faecalis* (VRE), and *Staph. epidermidis*.

The present invention includes a kit comprising the pharmaceutical composition or a glycopeptide antibiotic of the present invention and written instructions for its use in inhibition, delay of formation, treatment, prophylaxis and/or prevention of a slow growing, stationary-phase or biofilm bacterial infection, in a suitable container.

EXAMPLES

Bacterial Strains

The strains used in the experiments described herein were the MSSA reference strain ATCC 29213, the MRSA isolates ATCC 33591 and ATCC 43300, and the VRSA isolate VRS5 (Network on Antimicrobial Resistance in *Staphylococcus aureus* [NARSA]). MSSA ATCC 29213, MRSA ATCC 33591 and ATCC 43300 were grown overnight to stationary-phase in cation-adjusted Mueller Hinton broth (CAMHB; Becton, Dickinson and Company, Sparks, Md.) at 37° C. with rotation at 225 rpm. VRSA VRS5 was grown overnight to stationary-phase at 37° C. with rotation at 225 rpm in brain-heart infusion broth (Becton, Dickinson and Company) containing 4 µg/ml of vancomycin.

Nutrient-Depleted CAMHB

Nutrient-depleted CAMHB from each respective strain was prepared by 3 rounds of inoculation of CAMHB with exponential-phase bacteria, incubation overnight at 37° C. with rotation (225 rpm) and centrifugation (8000×g for 30 minutes) to remove bacteria. After the final round of inoculation, growth and centrifugation, the pH of the nutrient-depleted CAMHB was adjusted to pH=7.0 and the spent medium was filter-sterilized using a 0.22 µM membrane (Corning Incorporated, Corning, N.Y.).

Antibacterial Agents and Concentrations

Antibacterial agents were tested at pharmacokinetically-relevant concentrations that have been determined from clinical studies. Concentrations were chosen to approximate free peak ($fC_{max}$) and free trough levels in plasma following administration of standard doses in humans. For oritavancin, $fC_{max}$ and free trough levels from a standard dose of 200 mg (44) were used as well as an additional concentration that approximates the $fC_{max}$ following a single 800 mg dose ($fC_{max\ 800}$) in humans (15). Oritavancin diphosphate powder was dissolved in water containing 0.002% polysorbate-80; polysorbate-80 was also maintained at 0.002% in assays to minimize oritavancin loss to the surface of vessels (3) except where indicated. Concentrations that approximate the $fC_{max}$ and free trough levels in plasma, when administered at standard dosages, for the prototypical glycopeptide vancomycin, the oxazolidinone linezolid, and the lipopeptide daptomycin were determined from pharmacokinetic data and protein binding values of the respective package inserts (vancomycin, Vancocin®; linezolid, Zyvox®; daptomycin, Cubicin®). The approximation of the rifampicin $fC_{max}$ was derived from Burman et al, 2001 (5).

Example 1

Nutrient-depleted CAMHB Maintains the Viability of Stationary-Phase Cells

Stationary-phase bacteria inoculated into nutrient-depleted CAMHB (26) were used to model bacteria that are dividing slowly and dormant to antimicrobial agents. Inoculation of nutrient-depleted CAMHB with approximately $5 \times 10^7$ CFU/mL of stationary-phase cells of *S. aureus* ATCC 29213 resulted in limited growth over a 24 hour period: CFU/mL increased by approx 0.6 log (FIG. 1A). In contrast, exponential-phase cell density increased by approx 1.3 log over a 24 hour period (FIG. 1B). Nutrient-depleted CAMHB therefore limits the growth of stationary-phase inocula over a 24-hour period and allows for the monitoring of the action of antimicrobial agents against slow-growing bacteria.

Example 2

Oritavancin Retains Activity Against Stationary-phase *S. aureus*

Time-kill studies were performed to determine whether growth phase affects the antibacterial action of oritavancin and comparator agents.

Materials and Methods

Nutrient-depleted CAMHB containing diluted antimicrobial agents was inoculated with stationary-phase bacteria from overnight cultures of the *S. aureus* strains at approximately $10^7$ colony-forming units (CFU)/mL. Other experiments compared the killing of stationary- and exponential-phase *S. aureus* ATCC 29213 when inoculated into nutrient-depleted CAMHB containing the test agents. For assays involving daptomycin, nutrient-depleted CAMHB was supplemented with 50 µg/ml $CaCl_2$ (8). All time-kill studies were performed in 96-well deep-well plates at 37° C. with rotation (225 rpm) in a total volume of 750 µL. Bacteria were enumerated by serial-dilution plating. Bacteriostatic and bactericidal activity of the antimicrobial agents were defined as a reduction in viable cell counts of <3 or ≥3 log at 24 hours relative to the starting inoculum, respectively (33). Experiments were repeated at least three times and produced similar results; results from one experiment are presented.

Short duration (2 h) time-kill studies were performed in membrane assay buffer (see below) to characterize the killing of *S. aureus* ATCC 29213 under conditions used in the membrane depolarization and permeability assays. Exponential- and stationary-phase *S. aureus* ATCC 29213 cells were diluted to an $OD_{600}$=0.005 (approx $10^6$ CFU/mL) in membrane assay buffer (10 mM HEPES-Cl, pH 7.5, 50 µg/mL $CaCl_2$) with or without 5 mM glucose, respectively. Experiments were initiated by the addition of antimicrobial agents at the indicated concentrations and bacteria were enumerated by serial-dilution plating. Oritavancin was tested in the absence of polysorbate-80 in this assay as it interfered with fluorescence determinations in membrane assays (data not shown). Experiments were repeated three times and produced similar results; results from one assay are presented.

Results

In the first experiment, killing of stationary-phase MSSA ATCC 29213 (FIG. 1A) was compared to killing of an exponential-phase inoculum (FIG. 1B) in nutrient-depleted CAMHB. Estimated $fC_{max}$ levels of oritavancin, vancomycin and daptomycin were bactericidal against exponential-phase MSSA ATCC 29213 in nutrient-depleted CAMHB at the 24-hour time point (FIG. 1B). In contrast, only oritavancin retained bactericidal activity against the stationary-phase MSSA ATCC 29213 in nutrient-depleted CAMHB (FIG. 1A); all other agents exhibited reduced antibacterial activity with vancomycin being most affected by growth phase (approx 2.4-log less killing activity against stationary-phase cells compared to exponential-phase cells at the 24 hour time point). The estimated free-trough concentration derived from a 200 mg dose of oritavancin in humans (0.5 µg/mL) nearly achieved bactericidal levels (approx 2.9-log; FIG. S1) against stationary-phase MSSA at the 24-hour time point whereas free-trough concentrations of vancomycin and daptomycin were only bacteriostatic (FIG. 1C).

Figure 2:
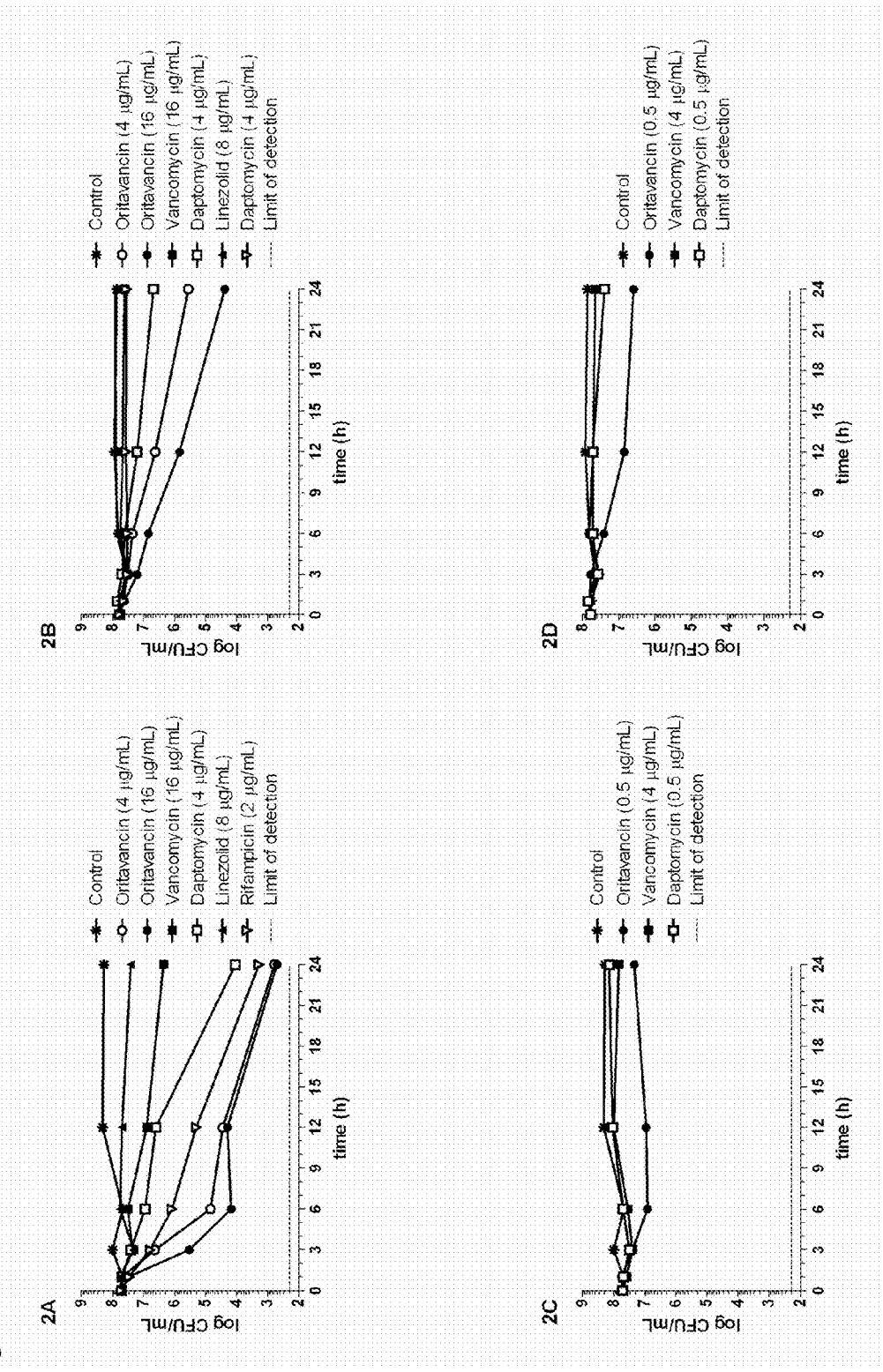
FIG. 2. Time-kill kinetics of stationary-phase MRSA ATCC 33591 and VRSA VRS5 at estimated $fC_{max}$ and free trough concentrations of oritavancin and comparators in nutrient-depleted CAMHB. Viability was enumerated at the indicated time points by serial dilution plating. Each point represents the mean of duplicate determinations. The limit of detection is indicated (- - -). A. MRSA ATCC 33591 with estimated $fC_{max}$ of oritavancin and comparators. B. VRSA VRS5 with estimated $fC_{max}$ of oritavancin and comparators. For panels A and B: *, growth control; ○, 4 μg/mL oritavancin; ●, 16 μg/mL oritavancin; ■, 16 μg/mL vancomycin; □, 4 μg/mL daptomycin; ▲, 8 μg/mL linezolid; ▽, 2 μg/mL rifampicin. C. MRSA ATCC 33591 with estimated free trough concentrations of oritavancin and comparators. B. VRSA VRS5 with estimated free trough concentrations of oritavancin and comparators. For both panels: *, growth control; ●, 0.5 μg/mL oritavancin; ■, 4 μg/mL vancomycin; □, 0.5 μg/mL daptomycin.

In a follow-up experiment, the killing of stationary-phase inocula of MRSA and VRSA in nutrient-depleted CAMHB were determined (FIG. 2). As was seen with MSSA, limited growth of MRSA ATCC 33591 (approx 0.6-log increase; FIG. 2A) and VRSA VRS5 (approx 0.1-log increase; FIG. 2B) occurred in nutrient-depleted CAMHB over 24 hours. Oritavancin exhibited concentration-dependent bactericidal activity against the MRSA and VRSA strains: oritavancin at its $fC_{max}$ and $fC_{max\ 800}$ was bactericidal at the 24-hour time point (FIG. 2) with the exception of the $fC_{max}$ against VRS5 (FIG. 2B) which was bacteriostatic (approx 2.2-log decrease). Vancomycin exhibited bacteriostatic activity against the stationary-phase inocula of MRSA and VRSA in nutrient-depleted CAMHB after 24 hours (FIG. 2). Daptomycin and rifampicin exhibited bactericidal activity at their respective $fC_{max}$ against the stationary-phase inoculum of MRSA (FIG. 2A) but were bacteriostatic against the VRSA strain (FIG. 2B). The bacteriostatic agent linezolid (31) had no effect on bacterial cell numbers of both strains over the 24-hour incubation. The estimated free-trough concentration of oritavancin (0.5 µg/mL) was bacteriostatic against the MRSA (approx 0.4-log reduction; FIG. 2C) and VRSA (approx 1.2-log reduction; FIG. 2D) strains. Similarly, free-trough concentrations of vancomycin and daptomycin were bacteriostatic against these isolates (FIGS. 2C and 2D).

Example 3

Oritavancin Perturbs Membrane Integrity of Stationary-phase *S. aureus*

Recent studies have demonstrated that oritavancin rapid bactericidal activity against exponential-phase *S. aureus* is temporally correlated with membrane depolarization and increased membrane permeability (30). To determine whether oritavancin also affects membrane energetics of stationary-phase cells, we explored the effects of oritavancin and comparator agents on membrane potential and permeability in stationary-phase MSSA ATCC 29213 using fluorescent probes.

Materials and Methods

Membrane depolarization was monitored using the fluorescent probe, 3,3'-dipropylthiadicarbocyanine iodide (($DiSC_3(5)$); Invitrogen Corporation, Carlsbad, Calif.), which partitions into the plasma membrane in proportion to the membrane potential. Dissipation of the membrane potential releases the probe leading to an increase in fluorescence. Previous studies with the glycopeptide telavancin (16) and the lipopeptide daptomycin (40) have used this probe to demonstrate the membrane perturbing activity of these drugs against exponential-phase cells. *S. aureus* ATCC 29213 was chosen for testing in membrane studies. Bacteria were grown overnight in CAMHB and sub-cultured the following day in CAMHB to exponential phase ($OD_{600}$≈0.25). Exponential- and stationary-phase cells were washed in membrane assay buffer with or without 5 mM glucose, respectively, and resuspended at an $OD_{600}$=0.25. $DiSC_3(5)$ was added to a final concentration of 1.5 µM and the solution was incubated in the dark at ambient temperature for 30 minutes to allow loading of the fluorescent dye into cell membranes. After the loading period, cells were diluted 50-fold ($OD_{600}$=0.005) in depolarization buffer with or without glucose for exponential- or stationary-phase cells, respectively. Assays were initiated by the addition of antimicrobial agents over a range of concentrations and were monitored in real time by fluorescence spectroscopy ($\lambda ex$=612, $\lambda em$=665) for a period of 30 minutes. Note that 0.002% polysorbate-80 was found to interfere with fluorescence in these assays and therefore was omitted from the assay. Experiments were repeated three times and produced similar results; results from one assay are presented.

For membrane permeability assays, bacteria were prepared identically as described above for the membrane depolarization assay with the exception that SYTO-9 and propidium iodide (Invitrogen Corporation) were added at 5 µM and 30 µM, respectively. Experiments were repeated three times and produced similar results; results from one assay are presented.

Results

Figure 3:
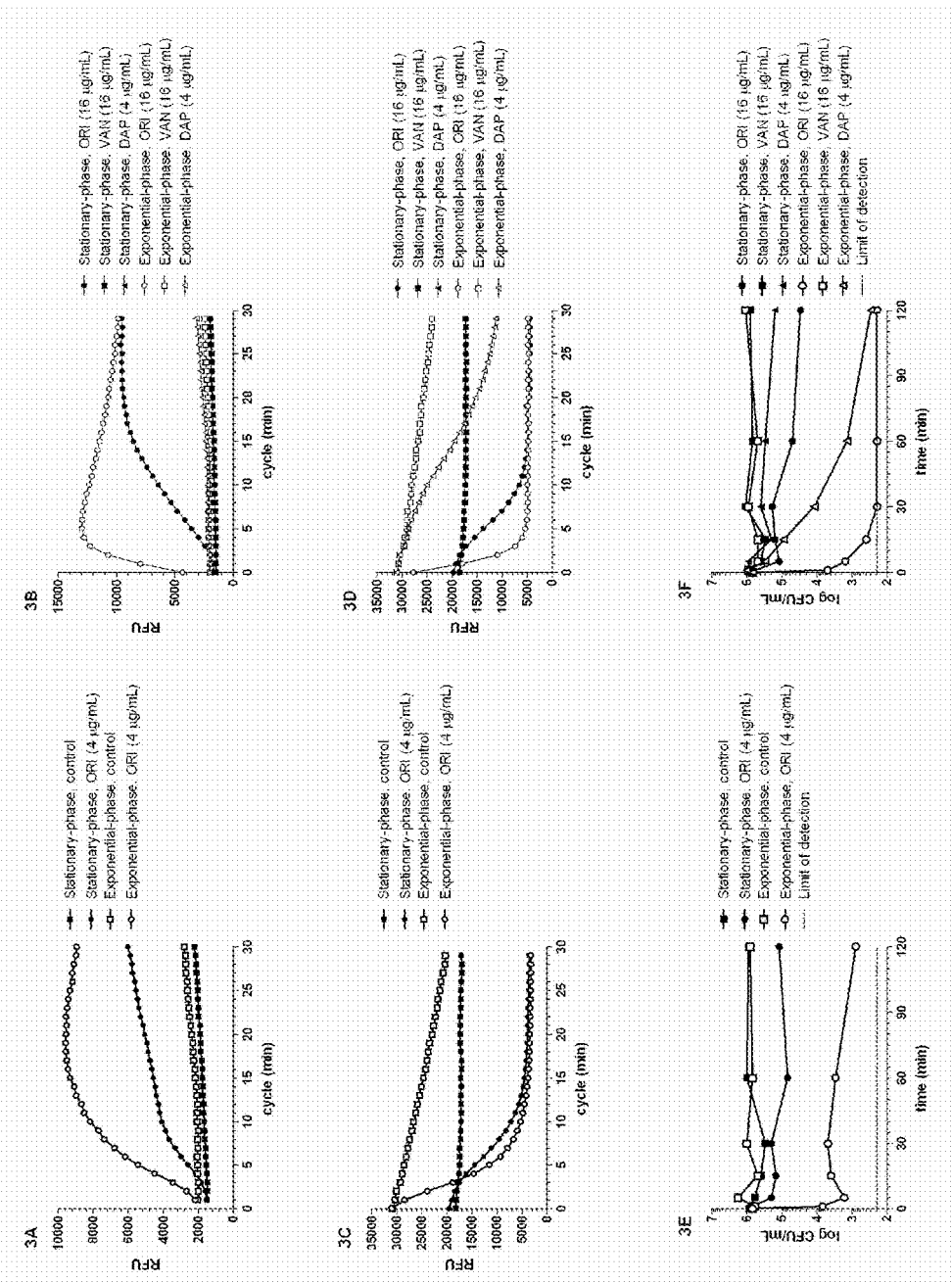
FIG. 3. Measurement of oritavancin effects on membrane depolarization, permeability and killing of MSSA ATCC 29213. Panels A and B. Membrane depolarization was monitored by measuring $DiSC_3(5)$ fluorescence. Panels C and D. Permeabilization of the cell membranes by oritavancin was monitored by measuring SYTO-9 fluorescence. Note that in panel D, the curve for vancomycin vs. stationary-phase cells overlaps the curve for daptomycin vs. stationary-phase cells. E. Killing kinetics of stationary- and exponential-phase inocula in membrane assay buffer. Glucose was omitted from the membrane assay buffer for stationary-phase cells and included at 5 mM for exponential-phase cells. The limit of detection is indicated (- - -). For panels A, C and E: ○, 4 μg/mL oritavancin vs. exponential-phase cells; ●, 4 μg/mL oritavancin vs. stationary-phase cells; □, untreated exponential-phase cells; ■, untreated stationary-phase cells. For panels B and D: ●, 16 μg/mL oritavancin vs. stationary-phase cells; ○, 16 μg/mL oritavancin vs. exponential-phase cells; ■, 16 μg/mL vancomycin vs. stationary-phase cells; □, 16 μg/mL vancomycin vs. exponential-phase cells; ▲, 4 μg/mL daptomycin vs. stationary-phase cells; △, 4 μg/mL daptomycin vs. exponential-phase cells.

Dissipation of membrane potential, measured as increased fluorescence resulting from the release of $DiSC_3(5)$ from stationary- and exponential-phase cell membranes, occurred in a concentration-dependent manner in response to oritavancin (FIG. 3A). However, the rate of release of the dye from stationary-phase cell membranes was less than that of exponential-phase cells. Addition of vancomycin had no effect on membrane potential, as indicated by the unchanged fluorescent signals that were comparable to the untreated control cells (FIG. 3B). Daptomycin exerted a small effect on the fluorescence of exponential-phase cells but did not effect changes on the stationary-phase inoculum within the time frame of the experiment (30 min; FIG. 3B) under the conditions described here.

In the membrane permeability assay, a quantitative difference in initial fluorescence was observed in stationary-phase cells compared to exponential-phase cells (FIG. 3C). This finding may reflect that stationary-phase cells either have a lower uptake of SYTO-9 or are initially more permeable to propidium iodide. Oritavancin increased membrane permeability of stationary-phase cells in a concentration-dependent manner (data not shown) as evidenced by decreases in SYTO-9 fluorescence (FIG. 3C). While the rate of loss of SYTO-9 fluorescence from stationary-phase cells was less than exponential-phase cells (FIG. 3C), vancomycin had no effect on fluorescence within the time frame of the assay (30 min; FIG. 3D). Daptomycin exposure caused loss of fluorescence from exponential-phase cells but had no effect on stationary-phase cells (FIG. 3D).

Time-kill studies over a short duration of exposure also showed that the rate of killing of stationary-phase MSSA by oritavancin was decreased compared to that of the exponential-phase inoculum (FIG. 3E). Rapid bactericidal activity of oritavancin against exponential-phase cells was exemplified by a 4-log reduction in CFU within 5 minutes when tested at 16 µg/mL, its predicted $fC_{max\ 800}$ in plasma from a single 800 mg dose. Rapid killing was also seen with the $fC_{max}$ of daptomycin (4 µg/mL; FIG. 3F). In contrast, stationary-phase cells exhibited approximately 1-log reduction in CFU within the 2-hour time period following exposure to oritavancin at the $fC_{max\ 800}$. Daptomycin activity was similarly affected as it exerted a 0.7-log reduction in CFU at its $fC_{max}$ (FIG. 3F). Vancomycin did not effect any change on bacterial counts of either inocula over the short time course of the assay (FIG. 3F).

Example 4

Oritavancin Targets the Septum of Stationary-phase MRSA ATCC

The effect of oritavancin on the ultrastructure of exponential-phase MRSA 43300 by transmission electron microscopy was recently studied, and septal deformations and loss of staining of the nascent septal cross wall, the 'mid-line' (28), in exposed cells was observed (A. Belley, B. Harris, T. Beveridge, T. Parr Jr and G. Moeck; submitted for publication). These effects were not seen following vancomycin exposure.

In a further study, stationary-phase MRSA ATCC 43300 ($5\times10^7$ CFU/mL) were exposed to 1 µg/mL oritavancin (2× its broth microdilution MIC in the absence of polysorbate-80) or 16 µg/mL vancomycin (16× its broth microdilution MIC) in nutrient-depleted CAMHB for 3 hours. Bacteria were fixed in 2.5% glutaraldehyde to cross-link proteins and help preserve morphological structure. Prior to embedding, the samples were treated with fresh 2.5% (vol/vol) glutaraldehyde in HEPES buffer (pH, 6.8) for 2 hours. The samples were then post-fixed in 2.0% (wt/vol) osmium tetroxide, followed by en bloc-staining with 2.0% (wt/vol) uranyl acetate, as a heavy-metal stain, to add contrast to the cells. The cells were then dehydrated through a series of ethanol washes then embedded in LR White resin. Once polymerized by curing, each culture sample was thin sectioned and stained by uranyl acetate and lead citrate so as to view the internal cellular constituents and the juxtaposition of cell envelope layers such as the plasma membrane and cell wall. Transmission electron microscopy was used to view the thin sections using a Philips CM10 under standard operating conditions at 100 kV.

Figure 4:
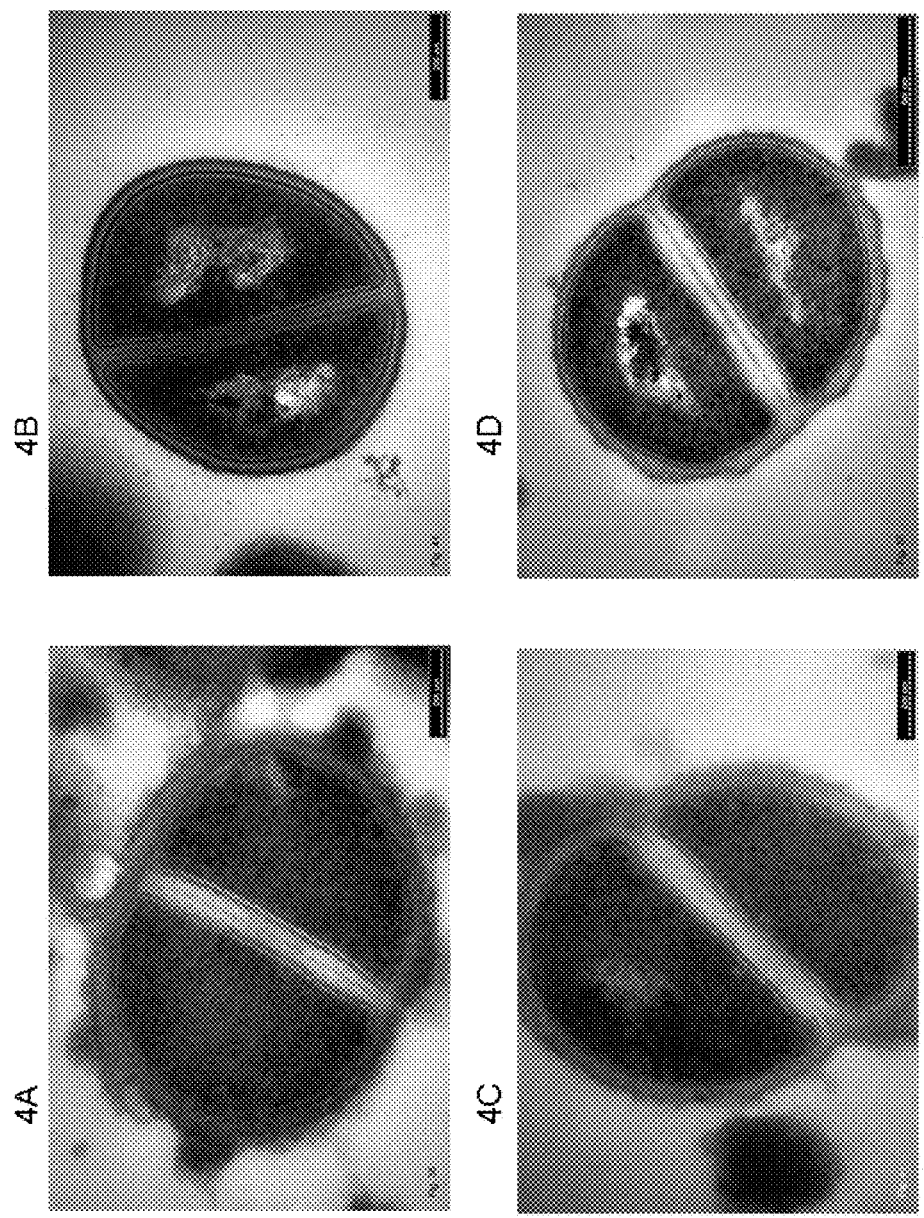
FIG. 4. Ultrastructural analysis of stationary-phase MRSA ATCC 43300 by transmission electron microscopy of thin sections. A. Untreated control cells. The arrow indicates the septal midline. B. An exponential-phase MRSA ATCC 43300 is shown for comparison. The septum is not as broad as in stationary-phase cells (compare to FIG. 4A) and the septal midline (arrow) is more apparent. C. Cells exposed to 1 μg/mL oritavancin for 3 hours. Note the absence of a well-defined midline. D. Cells exposed to 16 μg/mL vancomycin for 3 hours. The arrow indicates the septal midline.

Qualitative differences were evident upon examination of the stationary-phase culture compared to exponential-phase cells: cell ghosts were present but at a low frequency (data not shown), septa appeared broader (FIG. 4A) and the mid-line was apparent (FIG. 4A) but was not as distinct as in exponential-phase cells (FIG. 4B). Furthermore, an electron-dense material was present throughout the extracellular space and attached to the surface of stationary-phase cells (FIGS. 4A, 4C and 4D). Septa of oritavancin-treated cells were also broad but staining of the mid-line was conspicuously absent (FIG. 4C), corroborating observations in exponential-phase cells (data not shown). The midline was evident in vancomycin-treated cells (FIG. 4D), which overall had an ultrastructural appearance similar to the untreated cells.

Example 5

Oritavancin is Active Against In Vitro *S. aureus* Biofilms

The commercially-available MBEC™ system (Innovotech; Edmonton, AB, Canada) was used following the manufacturer's protocol (17) to establish in vitro biofilms of *S. aureus* and to determine the minimal biofilm eradication concentration (MBEC) of oritavancin and comparator antimicrobial agents. The MBEC represents the concentration of antimicrobial agent required to sterilize the biofilm after 24 hours of exposure. The MBEC™ system also allows for the determination of the minimal inhibitory concentration (MIC) of the test agent against planktonic cells under the conditions of the biofilm assay.

Material and Methods

150 µL of bacterial inocula at $10^7$ CFU/mL in tryptic soy broth was aliquoted into each well of an MBEC plate. Biofilms were established for 24 hours in a rotary incubator at 37° C. and 150 rpm. For experiments involving 72-hour biofilms, peg lids were transferred each day to 96-well plates containing 150 µL/well of fresh tryptic soy broth and incubated another 24 hours. Peg lids with established biofilms were washed once in sterile saline (200 µL/well) and then placed in plates containing antimicrobial agents diluted in CAMHB (200 μL/well). Antimicrobial agents were serially diluted in CAMHB in 96-well plates and peg lids were exposed for 24 hours or for the indicated times. Following antimicrobial challenge, peg lids were washed once in sterile saline then placed in recovery plates containing CAMHB (200 μL/well). The recovery plates were sonicated for 5 minutes in an ultrasonic sonicating bath (VWR Aquasonic model 550D) at the maximum setting then incubated for 24 hours and the MBECs recorded. MBECs were determined from at least three independent experiments; results represent the ranges of MBECs obtained. To enumerate the biofilm colony forming units (CFUs) on individual control pegs, pegs were broken off the lid using sterile forceps placed in 1 ml sterile saline, sonicated for 5 min and vortexed for 1 min at the highest setting. Bacteria were then enumerated by serial-dilution plating. CFU/peg counts were determined from at least three independent experiments; results presented are the average ±standard deviation.

To prevent loss of oritavancin due to binding to vessel surfaces (3), the CLSI now recommends inclusion of 0.002% polysorbate-80 for oritavancin broth microdilution MIC determinations (9). However, inclusion of polysorbate-80 during S. aureus biofilm establishment or antimicrobial challenge caused a significant reduction in CFU/peg densities (data not shown) and therefore it was omitted from MBEC determinations.

Results

In initial experiments, the capacity of each strain to form a biofilm on the pegs of the MBEC™ plate was determined by enumerating the CFU attached to the peg surface (CFU/peg). Cellular density on the pegs varied for each strain and ranged from means of $(2.9 \pm 2.4) \times 10^5$ CFU/peg for MSSA ATCC 29213, to $(2.2 \pm 1.7) \times 10^5$ CFU/peg for MRSA ATCC 33591 to $(2.6 \pm 1.1) \times 10^5$ CFU/peg for VRSA VRS5 after 24 hour of incubation. Planktonic MICs determined for comparator antimicrobial agents in the MBEC™ assay were within the CLSI quality control ranges (Table 1). Oritavancin planktonic MIC were also within quality control range (0.5-2 μg/mL) for MSSA ATCC 29213 determined in the absence of 0.002% polysorbate-80 (10). Growth of S. aureus in a biofilm caused dramatic decreases in the antimicrobial activity of vancomycin and linezolid as measured by the concentration of antimicrobial agent needed to sterilize the 24-hour biofilm (MBEC) compared to its respective planktonic MIC (Table 1): MBECs for both agents were >128 μg/mL against all three strains. In contrast, oritavancin MBECs ranged from 2-8 μg/mL against the S. aureus strains (Table 1) and were within one doubling dilution of their respective planktonic MICs in each experiment.

The time required for oritavancin to sterilize the 24-hour biofilm of MSSA ATCC 29213 was determined by determining the MBECs after shorter exposure times. Oritavancin sterilized the biofilm after a 1 hour exposure at an MBEC of 4 μg/mL. As expected, MBECs for the comparator agents were >128 μg/mL at this exposure time. To further test the ability of oritavancin to eradicate biofilm-associated S. aureus in vitro, biofilms of MSSA ATCC 29213 were grown for 72 hours to increase the cellular density of the peg biofilms. Indeed, CFU/peg increased to $(4.6 \pm 1.3) \times 10^6$ CFU/peg (approx 1.2 log increase compared to 24 hour biofilm cellular density) and oritavancin planktonic MIC and MBEC values were concomitantly affected, ranging from 4-32 μg/mL and 8-32 μg/mL, respectively. Importantly, within each experiment, oritavancin MBECs were no more than one doubling dilution higher than their respective planktonic MICs. Planktonic MICs for vancomycin and linezolid were also affected by the increased cellular peg density and were 2-16 μg/mL and 8-16 μg/mL, respectively. MBECs for both agents were >128 μg/mL.

Example 6

Oritavancin Sterilizes In Vitro Biofilms of Staphylococcus epidermidis and Vancomycin-susceptible and -Resistant Enterococci The ability of oritavancin (ORI) to eradicate biofilms of Staphylococcus epidermidis and vancomycin susceptible- and resistant enterococci, which are prominent in infections of indwelling devices and infective endocarditis, respectively, was determined.

Materials and Methods

The following strains were used for in vitro biofilm studies: vancomycin (VAN)-susceptible Enterococcus faecalis ATCC 29212 (VSE), VAN-resistant E. faecalis ATCC 51299 (VanB VRE), E. faecium ATCC 51559 (VanA VRE), S. epidermidis ATCC 12228 and the slime-producing strain S. epidermidis ATCC 35984. Biofilms were established in MBEC™ Physiology & Genetics Assay plates (Innovotech; Edmonton, Canada). Minimal biofilm eradication concentrations (MBEC) values for single antimicrobial agents (ORI, VAN, linezolid [LIN]) and for agents in combination (ORI with moxifloxacin [MOX] or rifabutin [RFB]) were determined in three independent experiments.

Results

Biofilms of VSE, VanB VRE and VanA VRE were sterilized by ORI at MBECs of 2 to 4 mg/L following 24 h of drug challenge. In contrast, the VSE and VRE biofilms were tolerant to VAN and LIN, exhibiting MBEC values >128 mg/L for both agents. Biofilms of S. epidermidis ATCC 12228 were sterilized by ORI at an MBEC of 2 to 4 mg/L but also exhibited tolerance to VAN and LIN with MBECs >128 mg/L. Sterilization of S. epidermidis ATCC 35984 biofilms required combinations of ORI (MBEC of 4 mg/L) and MOX (MBEC of 4 mg/L), or ORI (MBEC of 4 mg/L) and RFB (MBEC of 0.125 mg/L).

TABLE 1

Oritavancin exhibits anti-biofilm activity in vitro against S. aureus strains of different resistance phenotypes

| Antimicrobial Agent | MSSA ATCC 29213 | | MRSA ATCC 33591 | | VRSA VRS5 | |
|---|---|---|---|---|---|---|
| | MIC[1] | MBEC[2] | MIC | MBEC | MIC | MBEC |
| Oritavancin[3] | 2 | 2-4 | 0.5-4 | 0.5-4 | 2-8 | 2-8 |
| Linezolid | 8 | >128 | 2-4 | >128 | 4-8 | >128 |
| Rifampicin | <0.02 | 4 | <0.03 | 0.25-4 | <0.03-0.06 | 4 |
| Vancomycin | 1 | >128 | 1-2 | ≥128 | >128 | >128 |

[1]MICs (μg/mL) were determined in MBEC™ plates and represent the antibacterial activity against planktonic cells shed from the peg biofilms.
[2]MBECs (μg/mL) were determined following the manufacturer's protocol.
[3]Oritavancin MICs and MBECs were determined in the absence of polysorbate-80.

Example 7

Prevention of Staphylococcus epidermidis ATCC 35984 In Vitro Biofilm Formation on Silicone Tubing Silicone tubing (0.040" inner-diameter by 0.085" outer-diameter by 0.023" wall thickness; VWR International) was cut into 1 cm lengths then cut longitudinally in half. Cut tubing pieces were sterilized overnight in 99% ethanol. Tubing pieces were rinsed in 2 ml of sterile water then incubated overnight at room temperature in 20 mg/ml of either oritavancin or chloroeremomycin solution in water. Control tubing pieces were incubated in water as described. The following day, tubing pieces were rinsed in 2 ml of water then incubated with *Staphylococcus epidermis* ATCC 35984 at an inoculum density of either $10^5$ CFU/ml or $10^7$ CFU/ml in tryptic soy broth at 37° C. with rotation at 150 rpm in a rotational incubator. Tubing pieces were rinsed in 2 ml of sterile physiologic saline and bacteria in the biofilm formed on the silicone tubing were recovered by sonicating the tubing pieces in 1 ml of sterile physiologic saline in a sonicating water bath (VWR Aquasonic model 550D).

Figure 5:
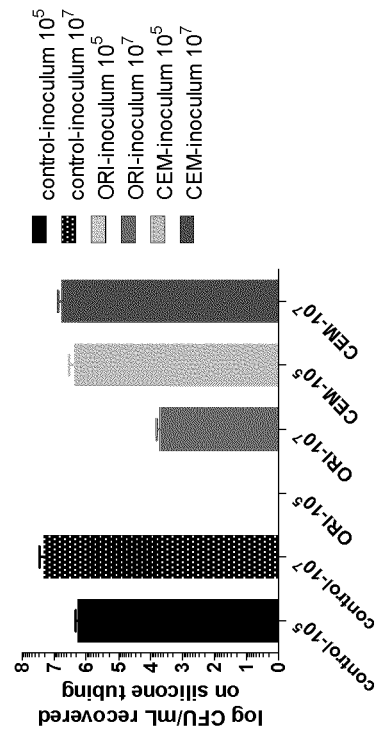
FIG. 5. Prevention of *Staph. epidermidis* ATCC 35984 in vitro biofilms formation on silicone tubing.

Recovered bacteria were enumerated by serial dilution plating. The results shown in FIG. 5 demonstrate the significant activity of oritavancin on a coated surface against biofilm formation.

Example 8

Prevention of *Staphylococcus epidermidis* Biofilm Formation on Polymeric Surface Derivatized with Oritavancin A] Preparation of Oritavancin Derivatized Beads with a Stable Linker.

1) Preparation of Attachment Precursor

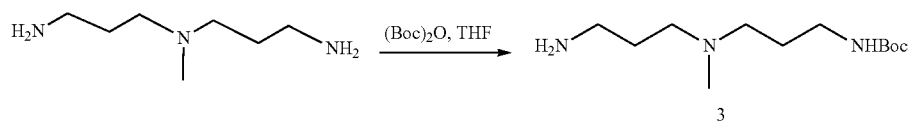

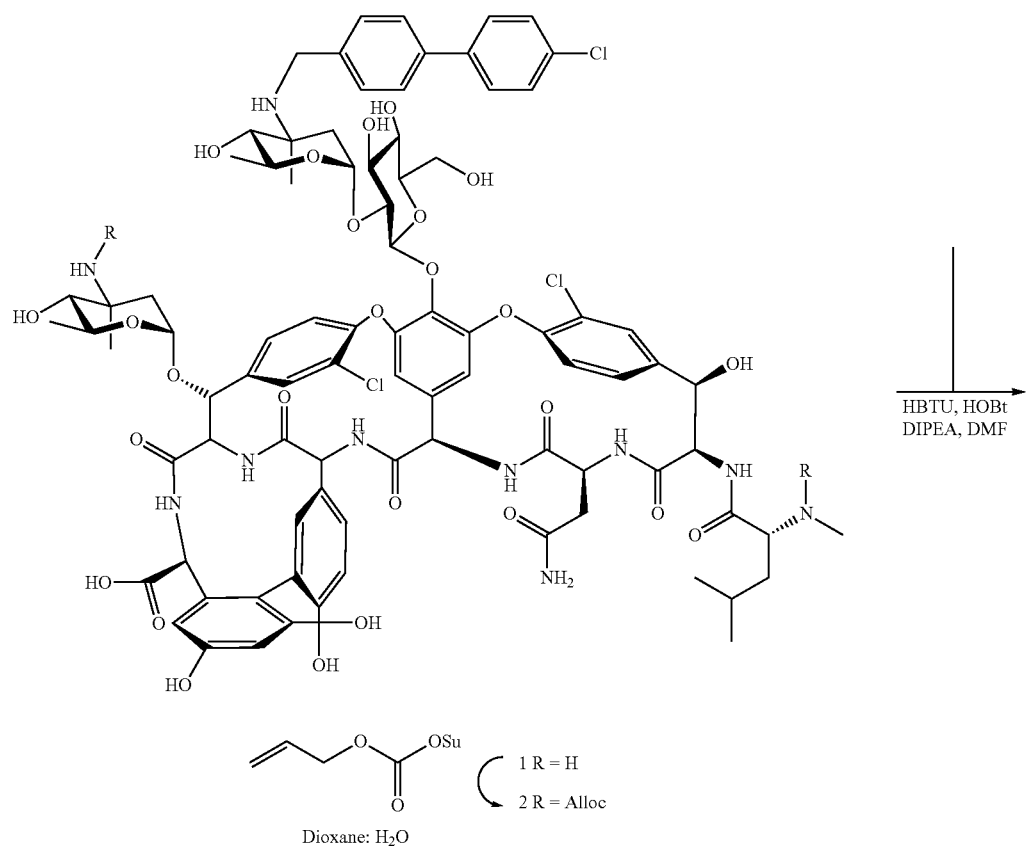

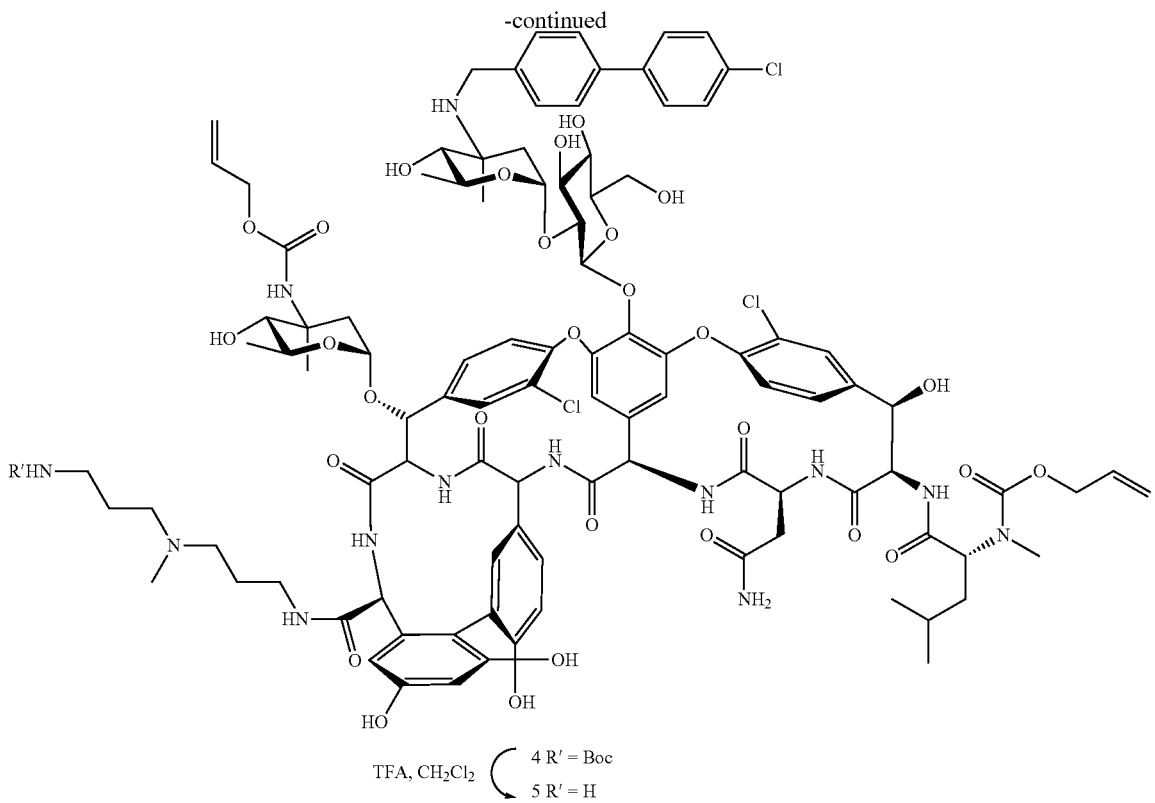

Di-N-Alloc oritavancin (2). To the bis(phosphoric acid) salt of oritavancin 1 (20.0 g, 10.05 mmol) in DMF (800 mL) and H$_2$O (200 mL) was added NaHCO$_3$ (6.75 g, 80.44 mmol) and the mixture was stirred until all of 1 had dissolved. A solution of Allyl N-succinimidyl carbonate (7.0 g, 35.2 mmol) in DMF (10 mL) was added and the resulting solution was stirred at room temperature for 20 h. The solvents were removed in vacuo, water was added and the pH was adjusted to 4.5 by the addition of aqueous 1N HCl. A mixture of acetone/Et$_2$O (1:3, 250 mL) was added, the solid was filtered, washed with H$_2$O and dried in vacuo to give 2 (20.84 g). ESI-MS: (M+H) calculated for C$_{94}$H$_{105}$Cl$_3$N$_{10}$O$_{30}$ 1961; found 1961.4.

tert-Butyl (7-amino-4-methyl-4-azaheptyl)carbamate (3). To a stirred solution of 3,3'-diamino-N-methyldipropylamine (22.0 g, 151.46 mmol) in THF (60 mL) cooled to 0° C. was added (Boc)$_2$O (10.9 g, 50.0 mmol) in THF (60 mL) over 2 h. After stirring for 18 h at room temperature, the mixture was concentrated to dryness in vacuo and the residue was partitioned between a saturated aqueous solution of NaCl (200 mL), and CH$_2$Cl$_2$ (400 mL). The organic phase was further washed with saturated brine (200 mL), dried over Na$_2$SO$_4$ and concentrated to dryness. The crude material was purified by silica gel chromatography on a Biotage Horizon™ flash chromatography system using a gradient of 5-70% methanol in 5% Et$_3$N/CH$_2$Cl$_2$ as the eluent to give 3 (10.1 g, 27%). $^1$H NMR (400 MHz, CDCl$_3$) δ 1.43 (s, 9H), 1.62 (m, 4H), 2.26 (s, 3H), 2.38 (t, 4H), 2.45 (bs, 3H), 2.78 (t, 3H), 3.16 (m, 2H).

Oritavancin derivative 4. A solution of 3 (6.89 g, 28.12 mmol) in DMF (20 ml) was added to a stirring solution of 2 (27.6 g, 14.07 mmol), HBTU (6.41 g, 16.89 mmol), HOBT (1.72 g, 16.89 mmol) and DIEA (3.67 mL, 21.07 mmol) in DMF (180 mL) cooled to in an ice-bath. The resulting mixture was stirred for 2 days at room temperature. It was concentrated to dryness in vacuo and a mixture of water and diethyl ether was added. The solid was filtered and washed copiously with diethyl ether. The crude product was purified by C18 reversed phase chromatography on a Biotage Horizon™ flash chromatography system using a gradient of 10-60% MeCN in 0.05% aqueous TFA as the eluent to give 4 (24.3 g, 78.9%). ESI-MS (M+H) calculated for C$_{106}$H$_{130}$Cl$_3$N$_{13}$O$_{31}$, 2188; found 2188.9.

Oritavancin derivative 5. A solution of 4 (24.3 g, 11.10 mmol) in CH$_2$Cl$_2$/TFA (300 mL, 2:1) at 0° C. was stirred for 2 h. The mixture was concentrated to dryness in vacuo and the crude product was purified by C18 reversed phase chromatography on a Biotage Horizon™ flash chromatography system using a gradient of 10-60% MeCN in 0.05% aqueous TFA as the eluent to give the TFA salt of 5 (7.1 g, 30.6%) as a colourless solid: ESI-MS calculated for C$_{101}$H$_{122}$Cl$_3$N$_{13}$O$_{19}$, 2088.34; found 2089.4 (M+H).

2) Resin Derivatization

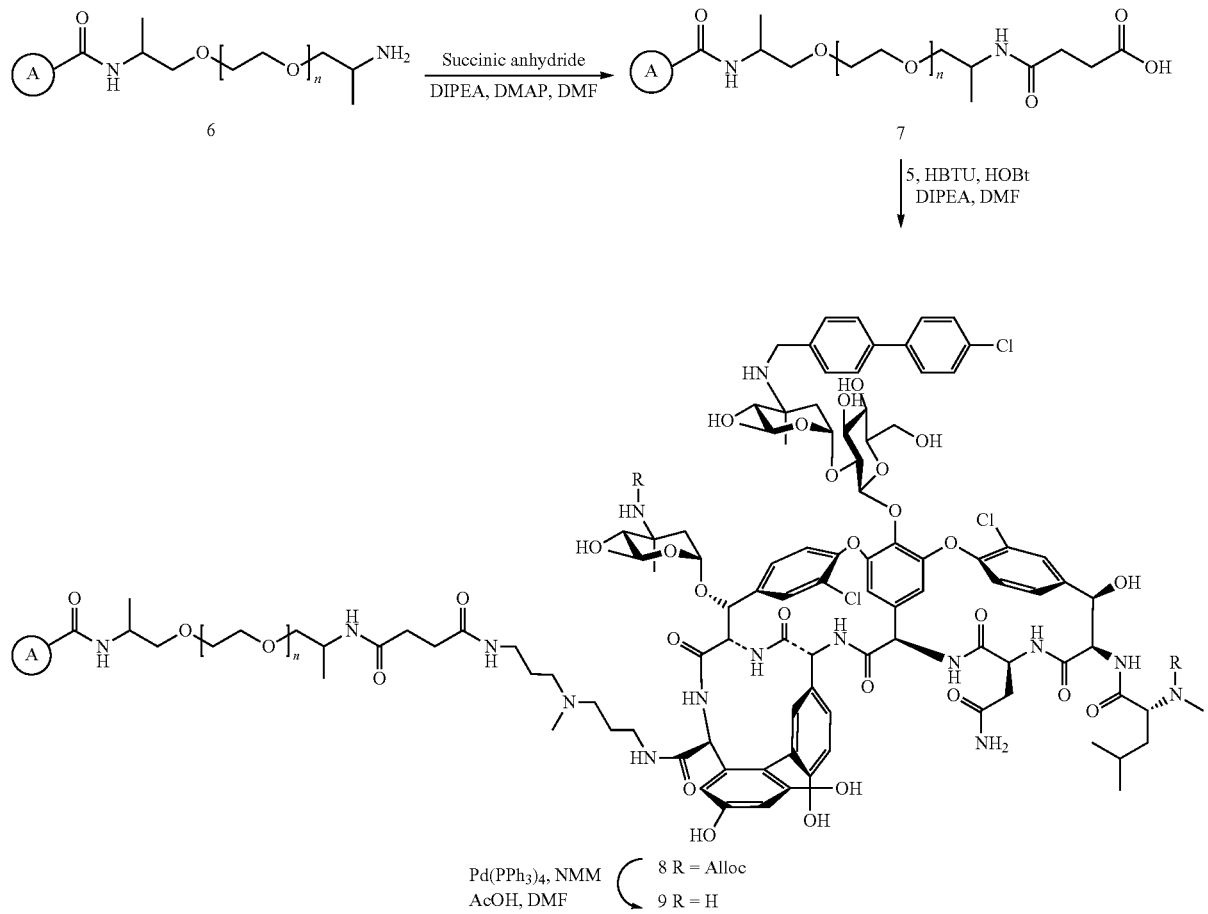

PL-PEGA succinamate 7. To PL-PEGA resin 6 (15 g, 0.4 mmol/g) swollen in DMF (150 mL) for 30 min in a solid phase synthesis flask was added succinic anhydride (2.56 g, 25.6 mmol), diisopropylethylamine (4.46 mL, 25.6 mmol) and 4-dimethylaminopyridine (1.45 g, 12.8 mmol). The mixture was gently agitated by a stream of Argon for 20 h and the resin was filtered, washed with DMF (2×100 mL) and $CH_2Cl_2$ (2×75 mL) and dried to give compound 7.

Oritavancin derivatized resin 8. A mixture of 5 (6.76 g, 3.24 mmol), resin 7 (3.0 g, 0.4 mmol/g), HOBt (0.486 g, 3.60 mmol), HBTU (1.36 g, 3.60 mmol) and diisopropylethylamine (1.04 mL, 6.0 mmol) in DMF (75 mL) in a solid phase synthesis flask was gently agitated by a stream of Argon for 24 h. The resin was filtered, washed with DMF (2×75 mL), $H_2O$ (2×100 mL) and MeOH (2×75 mL) and dried to give 8.

Oritavancin derivatized resin 9. $Pd(PPh_3)_4$ (6.76 g, 3.24 mmol), NMM (3.84 mL), and AcOH (7.7 mL, 3.60 mmol) were added to a suspension of resin 8 (3.0 g) in DMF (60 mL) in a solid phase synthesis flask. The mixture was gently agitated by a stream Argon for 2 days and the resin was filtered, washed with DMF (2×75 mL), $H_2O$ (2×100 mL) and MeOH (2×75 mL) and dried. It was loaded onto a Soxhlet and washed continuously with a 1:1 mixture of chloroform and methanol until the wash is free of materials (6 days). Elemental analysis: 54.79% C, 9.14% H, 3.23% N, which would suggest a loading of 113 mg of oritavancin base per g of polymer.

B] Preparation of Oritavancin Derivatized Beads with a Cleavable Linker.

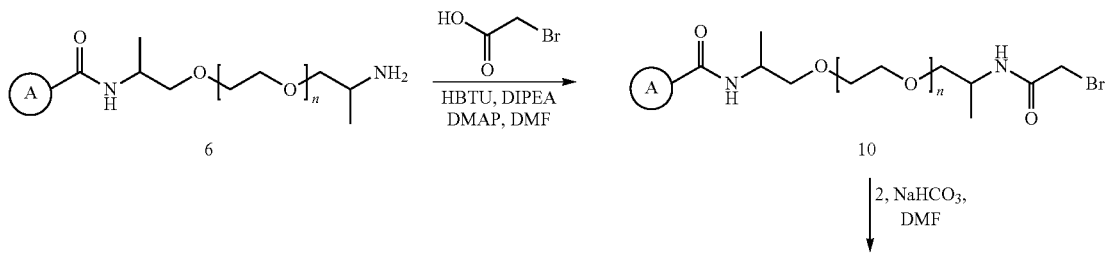

-continued

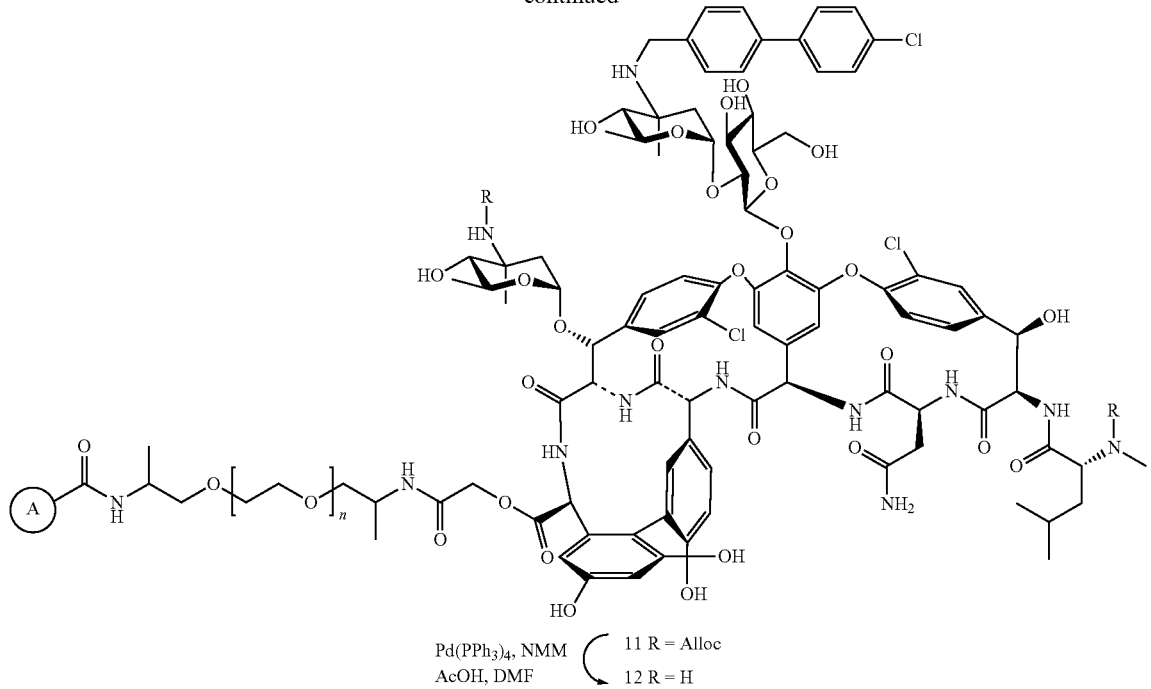

PL-PEGA bromoacetamide 10. To PL-PEGA resin 6 (4.0 g, 0.4 mmol/g) suspended in DMF (48 mL) for 30 min in a solid phase synthesis flask was added bromoacetic acid (1.11 g, 8.0 mmol), HBTU (3.03 g, 8.0 mmol), DMAP (195 mg, 1.6 mmol) and ethyldiisopropylamine (1.39 mL, 8.0 mmol). The mixture was gently agitated by a stream of argon for 18 h and the resin was filtered, washed with DMF (3×50 mL), $CH_2Cl_2$ (2×50 mL) and dried to give 10.

Oritavancin derivatized resin 11. Di-N-Alloc oritavancin (2, 9.41 g, 4.8 mmol), and $NaHCO_3$ (1.61 g, 19.2 mmol) in DMF (80 mL) were added to the resin 7 (4.0 g, 0.4 mmol/g) in DMF (50 mL) in a solid phase synthesis flask. The mixture was gently agitated by a stream of argon for 2 days and the resin was filtered, washed with DMF (2×75 mL), $H_2O$ (4×75 mL), $CH_2Cl_2$ (3×75 mL) and dried to give 11.

Oritavancin derivatized resin 12. $Pd(PPh_3)_4$ (1.85 g, 1.6 mmol), NMM (4.4 mL), and AcOH (8.8 mL)(1.36 g, 3.60 mmol) were added to the resin 11 (3.0 g, 0.4 mmol/g) suspended in DMF (70 mL) in a solid phase synthesis flask. The mixture was gently agitated by a stream of argon for 2 days and the resin was filtered, washed with DMF (3×100 mL), MeOH (2×50 mL), $CH_2Cl_2$ (3×75 mL) and dried. The resin was loaded on a Soxhlet extractor and was washed continuously with 50% $MeOH/CHCl_3$ until washes were free of contaminant (6 days). Complete deprotection of alloc group was confirmed by hydrolysis 100 mg of resin 12 with excess LiOH in $H_2O$ followed by LC-MS analysis. Elemental analysis: 55.25% C, 7.89% H, 5.51% N, which would suggest a loading of 477 mg of oritavancin base per g of polymer.

C] Determination of the Ability of *S. epidermidis* to Colonize the Resins.

Figure 6:
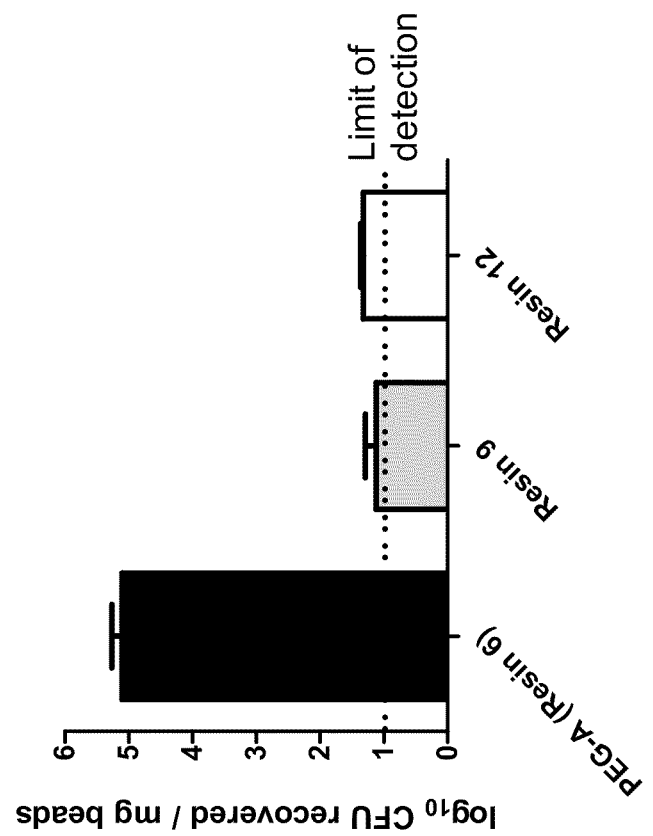
FIG. 6. Prevention of *Staph. epidermidis* ATCC 35984 in vitro biofilms formation on oritavancin derivatized resins 9 and 12

The impact of the presence of covalently linked oritavancin on the ability of bacteria to form a biofilm within the resin was determined as follows. Approximately 70 mg of each dry bead preparations were weighed into 15 ml snap-cap tubes then sterilized by soaking in 99% ethanol for 10 minutes. The beads were pelleted by centrifugation (900 g for 2 min) and the ethanol was decanted. The beads were then washed 5 times with sterile water. To establish biofilms, beads were resuspended in tryptic soy broth containing 1% glucose and with $4×10^4$ CFU/mg (dry bead weight) of *Staphylococcus epidermidis* ATCC 35984. The suspensions were then incubated overnight at 37° C. on a rotisserie. The beads were pelleted by brief centrifugation (50 g for 1 min) and the supernatants were decanted. The beads were washed twice with 10 ml sterile 0.85% saline and once with 3 ml sterile 0.85% saline. After the last wash, residual liquid remaining after decanting was aspirated using a pipette. The beads were then resuspended in 1 ml of saline and bacteria adhering to the bead surfaces (biofilm) were liberated by sonicating in an ultrasonic water bath for 5 min at the maximum setting. Viable bacteria were enumerated by serial dilution plating. The results are presented in FIG. 6.

The comparison of the large bacterial titer found in native PEG-A (resin 6) ($1.28×10^5 ± 5.62×10^4$ colony forming units per gram of resin) and the near sterility associated with resin 9 (13±6 colony forming units per gram of resin) and resin 6 (21±2 colony forming units per gram of resin) highlights the ability of covalently linked oritavancin to prevent the formation of *S. epidermidis* biofilms on this hydrophilic resin.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for in the recitation of the claims.

All documents, publications, patents, books, manuals, articles, papers, abstracts, posters and other materials referenced herein are expressly incorporated herein by reference in their entireties.

REFERENCES

1. Alborn, W. E., Jr., N. E. Allen, and D. A. Preston. 1991. Daptomycin disrupts membrane potential in growing *Staphylococcus aureus*. Antimicrob Agents Chemother 35:2282-7.
2. Allen, N. E., and T. I. Nicas. 2003. Mechanism of action of oritavancin and related glycopeptide antibiotics. FEMS Microbiol Rev 26:511-32.
3. Arhin, F., I. Sarmiento, A. Belley, G. McKay, D. Draghi, P. Grover, D. Sahm, T. R. Parr, Jr., and G. Moeck. 2008. Effect of Polysorbate-80 on Oritavancin Binding to Plastic Surfaces—Implications for Susceptibility Testing. Antimicrob Agents Chemother doi:10.1128/AAC.01513-07.
4. Arhin, F. F., I. Sarmiento, T. R. Parr, Jr, and G. Moeck. 2007. Effect of Polysorbate-80 on Oritavancin Binding to Plastice Surfaces-Implications for Susceptibility Testing, 17$^{th}$ European Congress of Clinical Microbiology and Infectious Diseases, Munich, Germany.
5. Burman, W. J., K. Gallicano, and C. Peloquin. 2001. Comparative pharmacokinetics and pharmacodynamics of the rifamycin antibacterials. Clin Pharmacokinet 40:327-41.
6. Ceri, H., M. E. Olson, C. Stremick, R. R. Read, D. Morck, and A. Buret. 1999. The Calgary Biofilm Device: new technology for rapid determination of antibiotic susceptibilities of bacterial biofilms. J Clin Microbiol 37:1771-6.
7. Ciampolini, J., and K. G. Harding. 2000. Pathophysiology of chronic bacterial osteomyelitis. Why do antibiotics fail so often? Postgrad Med J 76:479-83.
8. CLSI. 2006. Methods for Dilution Antimicrobial Susceptibility Tests for Bacteria That Grow Aerobically; Approved Standard, CLSI document M7-A7, 7th ed. Clinical and Laboratory Standards Institute, Wayne, Pa.
9. CLSI. 2008. Performance Standards for Antimicrobial Susceptibility Testing; Eighteenth Informational Supplement, CLSI document M100-S18, 7th ed. Clinical and Laboratory Standards Institute, Wayne, Pa.
10. CLSI. 2006. Performance standards for antimicrobial susceptibility testing; sixteenth informational supplement, CLSI document M100-S16, 7th ed. Clinical and Laboratory Standards Institute, Wayne, Pa.
11. Coates, A., Y. Hu, R. Bax, and C. Page. 2002. The future challenges facing the development of new antimicrobial drugs. Nat Rev Drug Discov 1:895-910.
12. Costerton, J. W., P. S. Stewart, and E. P. Greenberg. 1999. Bacterial biofilms: a common cause of persistent infections. Science 284:1318-22.
13. Donlan, R. M., and J. W. Costerton. 2002. Biofilms: survival mechanisms of clinically relevant microorganisms. Clin Microbiol Rev 15:167-93.
14. El-Azizi, M., S. Rao, T. Kanchanapoom, and N. Khardori. 2005. In vitro activity of vancomycin, quinupristin/dalfopristin, and linezolid against intact and disrupted biofilms of staphylococci. Ann Clin Microbiol Antimicrob 4:2.
15. Fetterly, G. J., C. M. Ong, S. M. Bhavnani, J. S. Loutit, S. B. Porter, L. G. Morello, P. G. Ambrose, and D. P. Nicolau. 2005. Pharmacokinetics of oritavancin in plasma and skin blister fluid following administration of a 200-milligram dose for 3 days or a single 800-milligram dose. Antimicrob Agents Chemother 49:148-52.
16. Higgins, D. L., R. Chang, D. V. Debabov, J. Leung, T. Wu, K. M. Krause, E. Sandvik, J. M. Hubbard, K. Kaniga, D. E. Schmidt, Jr., Q. Gao, R. T. Cass, D. E. Karr, B. M. Benton, and P. P. Humphrey. 2005. Telavancin, a multifunctional lipoglycopeptide, disrupts both cell wall synthesis and cell membrane integrity in methicillin-resistant *Staphylococcus aureus*. Antimicrob Agents Chemother 49:1127-34.
17. Innovotech. The MBEC™ Physiology & Genetics Assay: instruction manual Innovotech Inc, Edmonton Canada.
18. Jones, S. M., M. Morgan, T. J. Humphrey, and H. Lappin-Scott. 2001. Effect of vancomycin and rifampicin on meticillin-resistant *Staphylococcus aureus* biofilms. Lancet 357:40-1.
19. Kadurugamuwa, J. L., L. V. Sin, J. Yu, K. P. Francis, R. Kimura, T. Purchio, and P. R. Contag. 2003. Rapid direct method for monitoring antibiotics in a mouse model of bacterial biofilm infection. Antimicrob Agents Chemother 47:3130-7.
20. Kashket, E. R. 1981. Proton motive force in growing *Streptococcus* lactis and *Staphylococcus aureus* cells under aerobic and anaerobic conditions. J Bacteriol 146:369-76.
21. Kemper, M. A., M. M. Urrutia, T. J. Beveridge, A. L. Koch, and R. J. Doyle. 1993. Proton motive force may regulate cell wall-associated enzymes of *Bacillus subtilis*. J Bacteriol 175:5690-6.
22. Lefort, A., A. Saleh-Mghir, L. Garry, C. Carbon, and B. Fantin. 2000. Activity of LY333328 combined with gentamicin in vitro and in rabbit experimental endocarditis due to vancomycin-susceptible or -resistant *Enterococcus faecalis*. Antimicrob Agents Chemother 44:3017-21.
23. Lehoux, D., F. F. Arhin, I. Fadhil, K. Laquerre, V. Ostiguy, I. Sarmiento, G. Moeck, and T. R. Parr, Jr. 2006. Oritavancin Demonstrates Rapid and Sustained Bactericidal Activity in the Rat Granuloma Pouch Model of *Staphylococcus aureus* Infection, 46$^{th}$ Interscience Conference on Antimicrobial Agents and Chemotherapy, San Francisco, Calif.
24. Lewis, K. 2007. Persister cells, dormancy and infectious disease. Nat Rev Microbiol 5:48-56.
25. Lucet, J. C., M. Herrmann, P. Rohner, R. Auckenthaler, F. A. Waldvogel, and D. P. Lew. 1990. Treatment of experimental foreign body infection caused by methicillin-resistant *Staphylococcus aureus*. Antimicrob Agents Chemother 34:2312-7.
26. Mascio, C. T., J. D. Alder, and J. A. Silverman. 2007. Bactericidal action of daptomycin against stationary-phase and nondividing *Staphylococcus aureus* cells. Antimicrob Agents Chemother 51:4255-60.
27. Mates, S. M., E. S. Eisenberg, L. J. Mandel, L. Patel, H. R. Kaback, and M. H. Miller. 1982. Membrane potential and gentamicin uptake in *Staphylococcus aureus*. Proc Natl Acad Sci USA 79:6693-7.
28. Matias, V. R., and T. J. Beveridge. 2007. Cryo-electron microscopy of cell division in *Staphylococcus aureus* reveals a mid-zone between nascent cross walls. Mol Microbiol 64:195-206.
29. M$^c$Kay, G. A., S. Beaulieu, A. Belley, F. F. Arhin, T. R. Parr, Jr, and G. Moeck. 2007. In vitro Time Kill Studies of Oritavancin against Drug-resistant Isolates of *Staphylococcus aureus* and Enterococci, 47$^{th}$ Interscience Conference on Antimicrobial Agents and Chemotherapy, Chicago, Ill.
30. M$^c$Kay, G. A., I. Fadhil, S. Beaulieu, S. Ciblat, A. R. Far, G. Moeck, and T. R. Parr, Jr. 2006. Oritavancin Disrupts Transmembrane Potential and Membrane Integrity Concomitantly with Cell Killing in *Staphylococcus aureus*

31. Moellering, R. C. 2003. Linezolid: the first oxazolidinone antimicrobial Ann Intern Med 138:135-42.
32. Murillo, O., A. Domenech, A. Garcia, F. Tubau, C. Cabellos, F. Gudiol, and J. Ariza. 2006. Efficacy of high doses of levofloxacin in experimental foreign-body infection by methicillin-susceptible *Staphylococcus aureus*. Antimicrob Agents Chemother 50:4011-7.
33. NCCLS. 1999. Methods for Determining Bactericidal Activity of Antimicrobial Agents; Approved Guideline, NCCLS document M26-A National Committee for Clinical Laboratory Standards, Wayne, Pa.
34. Pinho, M. G., and J. Errington. 2005. Recruitment of penicillin-binding protein PBP2 to the division site of *Staphylococcus aureus* is dependent on its transpeptidation substrates. Mol Microbiol 55:799-807.
35. Rani, S. A., B. Pitts, H. Beyenal, R. A. Veluchamy, Z. Lewandowski, W. M. Davison, K. Buckingham-Meyer, and P. S. Stewart. 2007. Spatial patterns of DNA replication, protein synthesis, and oxygen concentration within bacterial biofilms reveal diverse physiological states. J Bacteriol 189:4223-33.
36. Rupp, M. E., P. D. Fey, and G. M. Longo. 2001. Effect of LY333328 against vancomycin-resistant *Enterococcus faecium* in a rat central venous catheter-associated infection model. J Antimicrob Chemother 47:705-7.
37. Saginur, R., M. Stdenis, W. Ferris, S. D. Aaron, F. Chan, C. Lee, and K. Ramotar. 2006. Multiple combination bactericidal testing of staphylococcal biofilms from implant-associated infections. Antimicrob Agents Chemother 50:55-61.
38. Saleh-Mghir, A., A. Lefort, Y. Petegnief, S. Dautrey, J. M. Vallois, D. Le Guludec, C. Carbon, and B. Fantin. 1999. Activity and diffusion of LY333328 in experimental endocarditis due to vancomycin-resistant *Enterococcus faecalis*. Antimicrob Agents Chemother 43:115-20.
39. Scheffers, D. J., and M. G. Pinho. 2005. Bacterial cell wall synthesis: new insights from localization studies. Microbiol. Mol Biol Rev 69:585-607.
40. Silverman, J. A., N. G. Perlmutter, and H. M. Shapiro. 2003. Correlation of daptomycin bactericidal activity and membrane depolarization in *Staphylococcus aureus*. Antimicrob Agents Chemother 47:2538-44.
41. Spoering, A. L., and K. Lewis. 2001. Biofilms and planktonic cells of *Pseudomonas aeruginosa* have similar resistance to killing by antimicrobials. J Bacteriol 183: 6746-51.
42. Svensson, E., H. Hanberger, and L. E. Nilsson. 1997. Pharmacodynamic effects of antibiotics and antibiotic combinations on growing and nongrowing *Staphylococcus epidermidis* cells. Antimicrob Agents Chemother 41:107-11.
43. Touhami, A., M. H. Jericho, and T. J. Beveridge. 2004. Atomic force microscopy of cell growth and division in *Staphylococcus aureus*. J Bacteriol 186:3286-95.
44. Van Bambeke, F., Y. Van Laethem, P. Courvalin, and P. M. Tulkens. 2004. Glycopeptide antibiotics: from conventional molecules to new derivatives. Drugs 64:913-36.
45. Wang, T.-S. A., D. Kahne, and S. Walker. 2007. Probing the mechanism of inhibition of bacterial peptidoglycan glycosyltransferases by glycopeptide analogs, 47th Interscience Conference on Antimicrobial Agents and Chemotherapy, Chicago, Ill.
46. Zheng, Z., and P. S. Stewart. 2004. Growth limitation of *Staphylococcus epidermidis* in biofilms contributes to rifampicin tolerance. Biofilms 1:31-35.
47. Rose, W. E., and P. T. Poppens. 2009. Impact of biofilm on the in vitro activity of vancomycin alone and in combination with tigecycline and rifampicin against *Staphylococcus aureus*. J Antimicrob Chemother 63:485-488.
48. Gander, S., Kinnaird, A. and R. Finch. 2005. Telavancin: in vitro activity against staphylococci in a biofilm model. J Antimicrob Chemother 56:337-343
49. Darouiche, R. O., and M. D. Mansouri. 2005. Dalbavancin compared with vancomycin for prevention of *Staphylococcus aureus* colonization of devices in vivo. Infect 50:206-209.

We claim:

1. A method of treating an infection caused by bacteria in biofilm form in a human subject in need thereof, wherein said method comprises administering a therapeutically effective amount of one or more antibiotics to the human subject having an infection caused by bacteria in biofilm form, wherein said one or more antibiotics comprises oritavancin or a pharmaceutically acceptable salt, hydrate or solvate thereof, or a mixture thereof, and wherein said treatment inhibits said infection in said subject by 100%.

2. The method of claim 1, wherein the administering is via intravenous administration or oral administration.

3. The method of claim 1, wherein said one or more antibiotics comprises a second antibiotic, and wherein the second antibiotic is administered concurrently with oritavancin or a pharmaceutically acceptable salt, hydrate or solvate thereof, or a mixture thereof.

4. The method of claim 3, wherein the second antibiotic is selected from the group consisting of fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifalazil, a rifalazil derived antibacterial agent, rifaximin and a rifaximin derived antibacterial agent.

5. The method of claim 4, wherein the rifamycin is rifampin, a rifampin derived antibacterial agent, rifabutin, a rifabutin derived antibacterial agent, rifapentin, or a rifapentin derived antibacterial agent.

6. The method of claim 1, wherein said one or more antibiotics is in the form of a pharmaceutical composition, and wherein the pharmaceutical composition further comprises a pharmaceutically acceptable carrier or diluent.

7. The method of claim 1, wherein the bacteria in biofilm form is selected from the group consisting of a vancomycin-susceptible enterococci, a vancomycin-resistant enterococci, a *Staphylococcus* species and a *Streptococcus* species.

8. The method of claim 1, wherein the bacteria in biofilm form is selected from the group consisting of vancomycin (VAN)-susceptible *Enterococcus faecalis* (VSE), VAN-resistant *E. faecalis* (VRE), *Staphylococcus epidermidis* and *Staphylococcus aureus*.

\* \* \* \* \*